US011435353B2

(12) United States Patent
Chen et al.

(10) Patent No.: US 11,435,353 B2
(45) Date of Patent: Sep. 6, 2022

(54) METHOD OF EVALUATING DRUG RESISTANCE AND TREATMENT EFFECT

(71) Applicant: National Cheng Kung University, Tainan (TW)

(72) Inventors: Pai-Sheng Chen, Tainan (TW); Jie-Ning Li, Tainan (TW); Yao-Lung Kuo, Tainan (TW); Ming-Yang Wang, Taipei (TW)

(73) Assignee: National Cheng Kung University, Tainan (TW)

( * ) Notice: Subject to any disclaimer, the term of this patent is extended or adjusted under 35 U.S.C. 154(b) by 866 days.

(21) Appl. No.: 16/209,907

(22) Filed: Dec. 4, 2018

(65) Prior Publication Data

US 2019/0277850 A1   Sep. 12, 2019

Related U.S. Application Data

(60) Provisional application No. 62/641,387, filed on Mar. 11, 2018.

(51) Int. Cl.
*G01N 31/00* (2006.01)
*G01N 33/53* (2006.01)
*G01N 33/574* (2006.01)
*A61K 31/138* (2006.01)

(52) U.S. Cl.
CPC ..... *G01N 33/57415* (2013.01); *A61K 31/138* (2013.01); *G01N 33/57488* (2013.01)

(58) Field of Classification Search
None
See application file for complete search history.

(56) References Cited

U.S. PATENT DOCUMENTS

2011/0223616 A1   9/2011   Atasoy

OTHER PUBLICATIONS

Frogne et al. (Endocrine-Related Cancer, 2005, vol. 12, pp. 599-614) (Year: 2005).*
Melo et al. (PNAS, Mar. 15, 2011, vol. 108, No. 11, pp. 4394-4399) (Year: 2011).*
Tove Kirkegaard et al., AKT activation predicts outcome in breast cancer patients treated with tamoxifen, Journal of Pathology, Aug. 9, 2005, pp. 139-146, XP002543643.
Xue Lin et al., Integrative analyses of gene expression and DNA methylation profiles in breast cancer cell line models of tamoxifen-resistance indicate a potential role of cells with stem-like properties, Breast Cancer Research, 2013, pp. 1-17, XP021175276.
G Pérez-Tenorio et al., Activation of AKT/PKB in breast cancer predicts a worse outcome among endocrine treated patients, British Journal of Cancer, 2002, Cancer Research UK, pp. 540-545, XP009513317.
Hani Goodarzi et al., Metastasis-suppressor transcript destabilization through TARBP2 binding of mRNA hairpins, Letter, Nature, vol. 513, Sep. 11, 2014, pp. 256-260, XP002791476.
Robert A. Smith et al., Cancer Screening in the United States, 2019: A Review of Current American Cancer Society Guidelines and Current Issues in Cancer Screening, CA Cancer J Clin 2019; 69:184-210, 2019.
Stephen RD Johnston, Acquired tamoxifen resistance in human breast cancer-potential mechanisms and clinical implications, Anti-Cancer Drugs, 1997, 8, pp. 911-930, 1997/08.
Mario Giuliano et al., Biological mechanisms and clinical implications of endocrine resistance in breast cancer, The breast 20, 2011, S3, Elsevier, S42-S49, 2011.
Elizabeth A. Musgrove et al., Biological determinants of endocrine resistance in breast cancer, Therapeutic Resistance, vol. 9, Sep. 2009, pp. 631-643, 2009/09.
F. Lumachi et al., Treatment of Estrogen Receptor-Positive Breast Cancer, Current Medicinal Chemistry, 2013, 20, pp. 596-604, 2013 Bentham Science Publishers, 2013.
Rebecca B. Riggins et al., Pathways to tamoxifen Resistance, Cancer Lett. Oct. 18, 2007; 256(1):1-24. doi:10.1016/j.canlet.2007.03.016, NIH Public Access, pp. 1-32, 2007.

\* cited by examiner

*Primary Examiner* — Lisa V Cook
(74) *Attorney, Agent, or Firm* — Winston Hsu

(57) ABSTRACT

The present invention provides a method of evaluating drug resistance in hormone therapy including the following steps. Firstly, a primary level of TRBP in a subject is measured, and an effective amount of tamoxifen, an active form of tamoxifen or an analogous of tamoxifen is provided to the subject. Then, a level of TRBP in the subject is measured after providing tamoxifen, the active form of tamoxifen or the analogous of tamoxifen. Finally, a level change of TRBP in the subject is discriminated to determine a tamoxifen resistance.

17 Claims, 35 Drawing Sheets

METHOD OF EVALUATING DRUG RESISTANCE AND TREATMENT EFFECT

CROSS REFERENCE TO RELATED APPLICATIONS

This application claims the benefit of priority of U.S. Provisional Application No. 62/641,387, filed on Mar. 11, 2018, which is incorporated herein by reference.

BACKGROUND OF THE INVENTION

1. Field of the Invention

The present invention related to a method of evaluating drug resistance and treatment effect, and more particularly to a method of evaluating drug resistance and treatment effect for breast cancer.

2. Description of the Prior Art

There are four cancers belong to female diseases in top ten cancers of women worldwide announced by ministry of health and welfare and WHO. Among them, breast cancer is the most common malignancy of women cancer and the treatment thereof remains failure. Based on the expression of estrogen receptor (ER) in tumor tissues, approximately 70% of breast cancers are ER positive (ER+) (Lumachi F et al., 2013). Theoretically, activation of the ER signaling pathway facilitates proliferation and tumorigenesis of breast cancer cells, and thus hormone therapy is the major treatment for ER+ breast cancer patients.

Tamoxifen is a selective estrogen-receptor modulator (SERM) that was discovered in 1967, and which has been the gold standard used in first line hormonal therapy for more than 45 years. Currently, tamoxifen is widely used to treat all stages of breast cancer and for chemoprevention in women at high risk for breast cancer. Despite that ER+ breast cancer exhibits a high initial response to hormonal therapy, drug resistance and cancer recurrence ultimately develop (Giuliano et al., 2011; Musgrove and Sutherland, 2009; Riggins et al., 2007), especially in metastatic breast cancer patients who are treated with tamoxifen (1998; Johnston, 1997; Smith et al., 2011). Clinical scenarios of drug resistance result from diverse mechanisms, and the early response to drug treatment for cancer depends on primary (de novo) resistance derived from the natural defensive ability of tumor cells. However, during treatment, cancer cells undergo clonal adaption, selection, and expansion into tumors with acquired resistance, which may also contribute to recurrence. Thus, it is urgent to identify the resistant mechanism to tamoxifen and to improve the conventional therapeutic scheme for breast cancer.

SUMMARY OF THE INVENTION

One object of the present invention is to provide a method of evaluating drug resistance for breast cancer, in which a TAR (HIV-1) RNA binding protein 2 (TRBP) level in a subject is measured and monitored to determine an acquired resistance and/or a primary resistance to tamoxifen treatment.

One object of the present invention is to provide a method of evaluating treatment effect for breast cancer, in which a TRBP level in a subject is measured and monitored to determine possible recurrences and poor prognosis after a hormone therapy.

To achieve the purpose described above, the present invention provides a method of evaluating drug resistance in hormone therapy including the following steps. Firstly, a primary level of TRBP in a subject is measured, and an effective amount of tamoxifen, an active form of tamoxifen or an analogous of tamoxifen is provided to the subject. Then, a level of TRBP in the subject is measured after providing tamoxifen, the active form of tamoxifen or the analogous of tamoxifen. Finally, a level change of TRBP in the subject is discriminated to determine a tamoxifen resistance.

To achieve the purpose described above, the present invention also provides a method of evaluating treatment effect in hormone therapy including the following steps.

In summary, the present invention has proved a novel phospho-AKT (p-AKT)-TRBP-SOX2 pathway induced by tamoxifen treatment which contributes not only to acquired resistance but also to de novo resistance, so that, a valuating method for a hormone therapy in breast cancer may be established thereby, through measuring and monitoring a level change of TRBP in a target subject to discriminate the acquired resistance and/or the novo resistance of the target subject, and also to further determine recurrence and/or poor prognosis of the target subject after a hormone therapy. In this way, the evaluating method of the present invention not only reveals a missing link between the tamoxifen-induced signaling network and tamoxifen resistance, but also further provides an important information for the design of better therapeutic approaches in breast cancer.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

FIG. 3A-3G are schematic diagrams illustrating dates to prove that TRBP is overexpressed in hormone therapy resistant cells and breast cancer tissues according to the present invention, in which:

FIG. 3A shows a western blot data for the expression of different microRNA biogenesis factors in cells;

FIG. 3B shows representative images of TRBP IHC in primary tumors and tumors in lymph nodes in cases of cancer recurrence;

FIG. 3C shows statistics of TRBP protein expression levels in primary tumors and metastatic tumor cells in cases of cancer recurrence;

FIG. 3D shows an expression of TRBP being analyzed and downloaded by using Oncomine;

FIG. 3E shows another expression of TRBP being analyzed and downloaded using Oncomine;

FIG. 3F shows a correlation of TARBP2 expression with overall survival in ER-positive breast cancer patients being analyzed and downloaded by using Kaplan-Meier Plotter; and FIG. 3G shows a correlation of TRBP expression with the prognosis of breast cancer patients being analyzed and downloaded by using PrognoScan.

FIGS. 4A-4J are schematic diagrams illustrating dates to prove elevated TRBP promotes acquired resistance to tamoxifen according to the present invention; in which:

FIGS. 4A and 4B show a western blot date and a MTT data of the TRBP expressions in a tamoxifen-resistant cell (MCF-7/TR);

FIGS. 4C and 4D show a western blot date and a MTT data of the TRBP expressions in a tamoxifen-resistant cell (MCF-7/TR2);

FIGS. 4E and 4F show a western blot date and a MTT data of the Dicer expressions in the tamoxifen-resistant cell (MCF-7/TR);

FIGS. 4G and 4H show a western blot date and a MTT data of the Dicer expressions in the tamoxifen-resistant cell (MCF-7/TR2); and FIGS. 4I and 4J show a western blot date and a MTT data of the TRBP expressions in a control, wt-TRBP, or ΔC4-TRBP plasmid.

FIGS. 5A-5E are schematic diagrams illustrating date to prove TRBP is induced by tamoxifen treatment in ER+ breast cancer cells according to the present invention; in which:

FIG. 5A shows a western blot date and a MTT data of the TRBP expressions in the tamoxifen-resistant cell (MCF-7/TR);

FIG. 5B shows another western blot date and another MTT data of the TRBP expressions in the tamoxifen-resistant cell (MCF-7/TR);

FIG. 5C shows a western blot date and a MTT data of the TRBP expressions in an ER+ breast cancer cell (ZR-75-1);

FIG. 5D shows another western blot date and another MTT data of the TRBP expressions in the ER+ breast cancer cell (ZR-75-1); and FIG. 5E shows a western blot date of the TRBP expressions in ER− breast cancer cells.

FIGS. 6A-6I are schematic diagrams illustrating date to prove tamoxifen-induced TRBP contributes to acquired resistance to tamoxifen according to the present invention, in which:

FIGS. 6A and 6D show western blot date for effect of TRBP on tamoxifen sensitivity in the tamoxifen-resistant cell (MCF-7/TR) and the ER+ breast cancer cell (ZR-75-1);

FIGS. 6B and 6E MTT data for effect of TRBP on tamoxifen sensitivity in the tamoxifen-resistant cell (MCF-7/TR) and the ER+ breast cancer cell (ZR-75-1);

FIG. 6C shows a colony formation data for effect of TRBP on tamoxifen sensitivity in the tamoxifen-resistant cell (MCF-7/TR) and the ER+ breast cancer cell (ZR-75-1);

FIG. 6F and FIG. 6H show western blot date for effect of Dicer expression on the tamoxifen-treated tamoxifen-sensitive cell (MCF-7) and the tamoxifen-treated ER+ breast cancer cell (ZR-75-1); and FIG. 6G and FIG. 6I show MTT date for effect of Dicer expression on the tamoxifen-treated tamoxifen-sensitive cell (MCF-7) and the tamoxifen-treated ER+ breast cancer cell (ZR-75-1).

FIGS. 7A-7I are schematic diagrams illustrating date to prove tamoxifen stabilizes TRBP through downregulation of Merlin, in which:

FIGS. 7A, 7B and 7C show a western blot data and a qRT-PCR data for tamoxifen enhanced the protein stability of TRBP; and FIGS. 7D, 7E, 7F, 7G, 7H, 7I show western blot data and MTT data for Merlin in tamoxifen sensitivity through regulation of TRBP.

FIGS. 8A-8K are schematic diagrams illustrating date to prove tamoxifen induces SOX2 to enhance tamoxifen resistance through TRBP, in which:

FIGS. 8A and 8B show a western blot data and a qRT-PCR data for expression of different stem cell markers after tamoxifen treatment;

FIGS. 8C and 8D show a western blot data and a MTT data for effect of SOX2 expression on tamoxifen sensitivity;

FIG. 8E Shows a colony formation data and a MTT data for proliferation;

FIGS. 8F, 8G, 8H and 8I show western blot data and reverse-transcription PCR data for tamoxifen downregulated SOX2 through TRBP; and FIGS. 8J and 8K show western blot data for upstream modulator of TRBP.

FIGS. 9A-9C are schematic diagrams illustrating date to prove SOX2 and TRBP expression are elevated in hormone therapy resistant tumor cells, in which:

FIG. 9A shows a correlation of SOX2 expression with the overall survival of patients with ER+ breast cancer; and FIGS. 9B and 9C show an association of SOX2 expression and hormone therapy resistance in breast cancer tissues.

DETAILED DESCRIPTION

Figure 1:
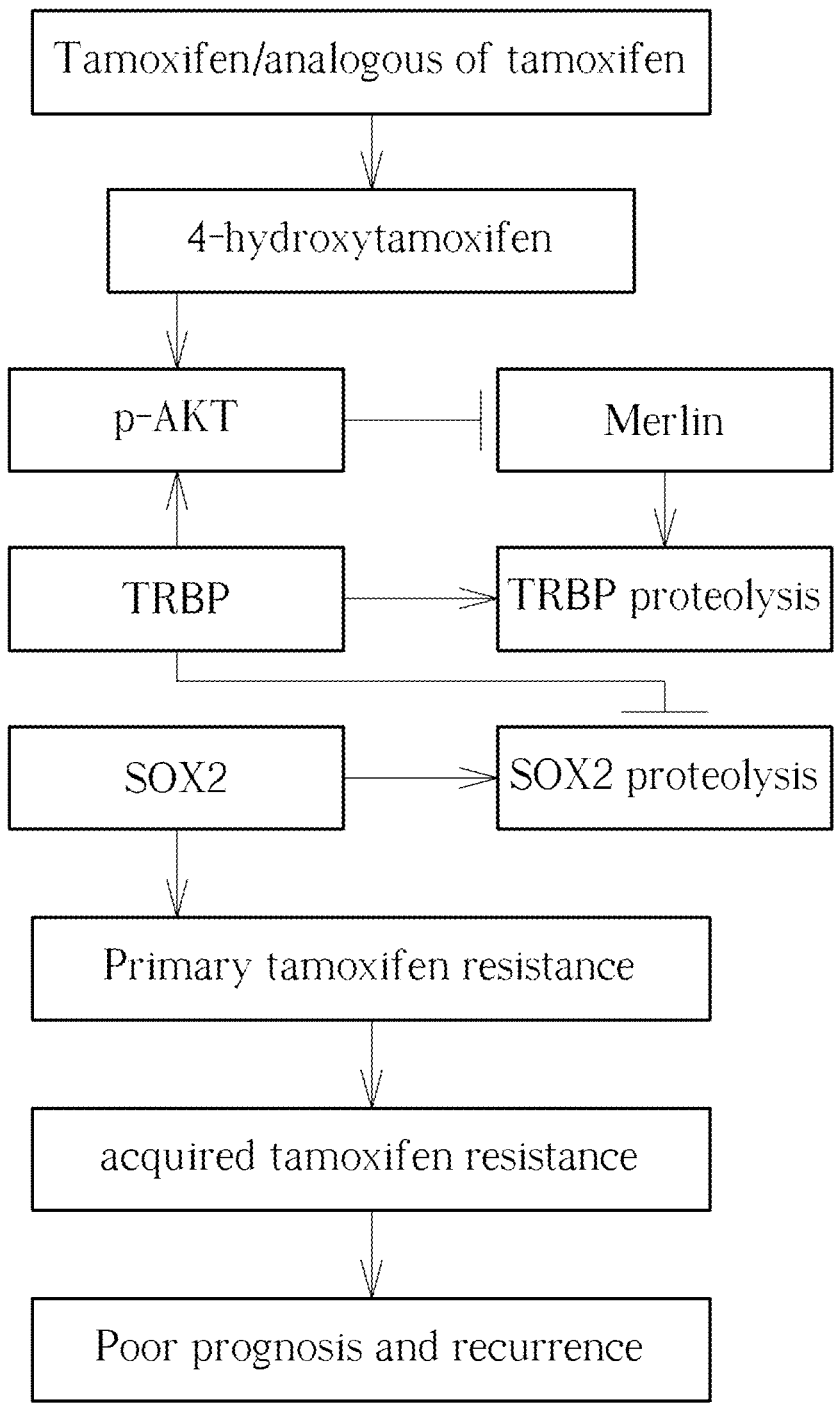
FIG. 1 is a schematic diagram illustrating a resistance mechanism for tamoxifen induced p-AKT-TRBP-SOX2 pathway according to the present invention.

To provide a better understanding of the presented invention, preferred embodiments will be made in detail. The preferred embodiments of the present invention are illustrated in the accompanying drawings with numbered elements.

The present invention mainly establishes an evaluating method for a hormone therapy such as a tamoxifen treatment in breast cancer, in which a level change of TAR (HIV-1) RNA binding protein 2 (TRBP) in a target subject is measured and monitored right before and after the tamoxifen treatment, so as to discriminate an acquired resistance and/or a primary resistance in the target subject, and also to further predict possible recurrence and/or poor prognosis of breast cancer in the target subject. In the present embodiment, the target subject may be a patient with breast cancer, such as an ER+ patient, any suitable samples like cells or body fluids taken from the aforementioned patient, or other suitable organisms.

Precisely speaking, the aforementioned evaluating method is established according to a novel p-AKT-TRBP-SOX2 pathway induced by tamoxifen treatment of the present invention, and which is accomplished by firstly administrating an effective amount of tamoxifen into the target subject, for example through any suitably administration like injection, oral administration or incubation. Preferably, the effective amount of tamoxifen is but not limited to be about 20-40 mg/per day. Next, a level of TRBP in the target subject is measured, in comparison with a primary level of TRBP in the target subject measured before the tamoxifen administration, with the level and the primary level of TRBP both referring to a TRBP protein level in the target subject, preferably. Then, the level change between the primary level and the level of TRBP in the target subject is monitored to discriminate an acquired resistance and/or a primary resistance in the target subject. For example, while the level of TRBP is higher than the primary level of TRBP in the target subject, such as being about 20% or more than 20% higher than the primary level of TRBP, the target subject is discriminated as the acquired resistance and/or the primary resistance. Also, while the level of TRBP is higher than the primary level of TRBP in the target subject, such as being about 20% or more than 20% higher than the primary level of TRBP, the target subject is discriminated to have recurrence and/or poor prognosis of breast cancer.

Furthermore, in one embodiment, the aforementioned evaluating method may be established by further measuring and monitoring a level change of p-AKT and/or SOX2 in the target subject, so as to facilitate the discrimination of the acquired resistance and/or the primary resistance, and the recurrence and/or poor prognosis of breast cancer in the target subject. Since p-AKT and/or SOX2 are respectively the functional upstream target and downstream target of the tamoxifen-TRBP axis, a level change of p-AKT and/or SOX2 in the target subject may also be measured after the tamoxifen administration, in comparison with a primary level of p-AKT and/or SOX2 in the target subject measured before the tamoxifen administration. Likewise, while the level of p-AKT and/or SOX2 is higher than the primary level of p-AKT and/or SOX2 in the target subject, such as being about 20% or more than 20% higher than the primary level of p-AKT and/or SOX2, the target subject may be further confirmed to have an acquired resistance and/or a primary resistance for tamoxifen, as well as recurrence and/or poor prognosis of breast cancer, in the target subject. Preferably, the level and the primary level of SOX2 are both related to a SOX2 protein level in the target subject. Then, the level change between the primary level and the level of p-AKT and/or SOX2 in the target subject is further used to ensure the discrimination of tamoxifen resistance, as well as poor prognosis.

Although the tamoxifen treatment of present embodiment is exemplified by administrating the effective amount of tamoxifen, the present invention is not limited thereto and may include other processes in order to meet the practical requirements. In one embodiment, the tamoxifen treatment may also be accomplished by administrating an effective amount of an active form of tamoxifen, such as 4-hydroxytamosifen (4OHT), or an effective amount of an analogous of tamoxifen to the subject, but is not limited thereto. Preferably, the effective amount of the active form of tamoxifen (such as 4OHT) may be about 20-40 mg/per day, but is not limited thereto.

Please refer to FIG. 1, FIG. 1 shows a schematic diagram illustrating the aforementioned p-AKT-TRBP-SOX2 pathway according to the present invention. In the present invention, a mechanism of tamoxifen resistance is identified in ER+ breast cancer cells through stabilization of TRBP protein and upregulation of a transcription factor SOX2. TRBP is an RNA binding protein that exhibits several known functions. At the molecular level, TRBP suppresses the activation of interferon (IFN)-induced dsRNA-regulated protein kinase PKR and interacts with the PKR activator PACT. TRBP also regulates HIV-1 gene expression through its interaction with TAR13 and is also involved in the RNAi/miRNA pathway as a cofactor that binds to Dicer in the RISC complex. Biologically, the role of TRBP in development was observed in TRBP knockout mice, which exhibit growth defects. The expression of TRBP enhances a transformed phenotype and tumorigenesis in vivo. In the present invention, we found that the expression of TRBP was dramatically upregulated in tamoxifen-resistant cells. Moreover, the induction of TRBP was found to be directly triggered by the tamoxifen treatment, which suggests a therapy-induced drug resistance pathway that should be considered when tamoxifen is used, as it provides crucial information for the development of possible therapeutic strategies.

The aforementioned p-AKT-TRBP-SOX2 pathway has been proved step by step via the following experiments, and materials and methods used in the following experiments are summarized in the following Materials and Methods paragraphs below. In the following experiments, we have proved that TRBP is overexpressed in hormone therapy resistant cells and breast cancer tissues, elevated TRBP promotes acquired resistance to tamoxifen, tamoxifen-induced TRBP results in the desensitization of ER+ breast cancer cells, tamoxifen posttranscriptionally stabilizes TRBP protein expression through downregulation of merlin, tamoxifen-induced TRBP stabilizes SOX2 protein to enhance desensitization of breast cancer cells to tamoxifen, and higher expression of SOX2 is correlated with the level of TRBP and hormone therapy resistance in breast cancer patients, sequentially.

I. TRBP is Overexpressed in Hormone Therapy Resistant Cells and Breast Cancer Tissues.

Figure 2:
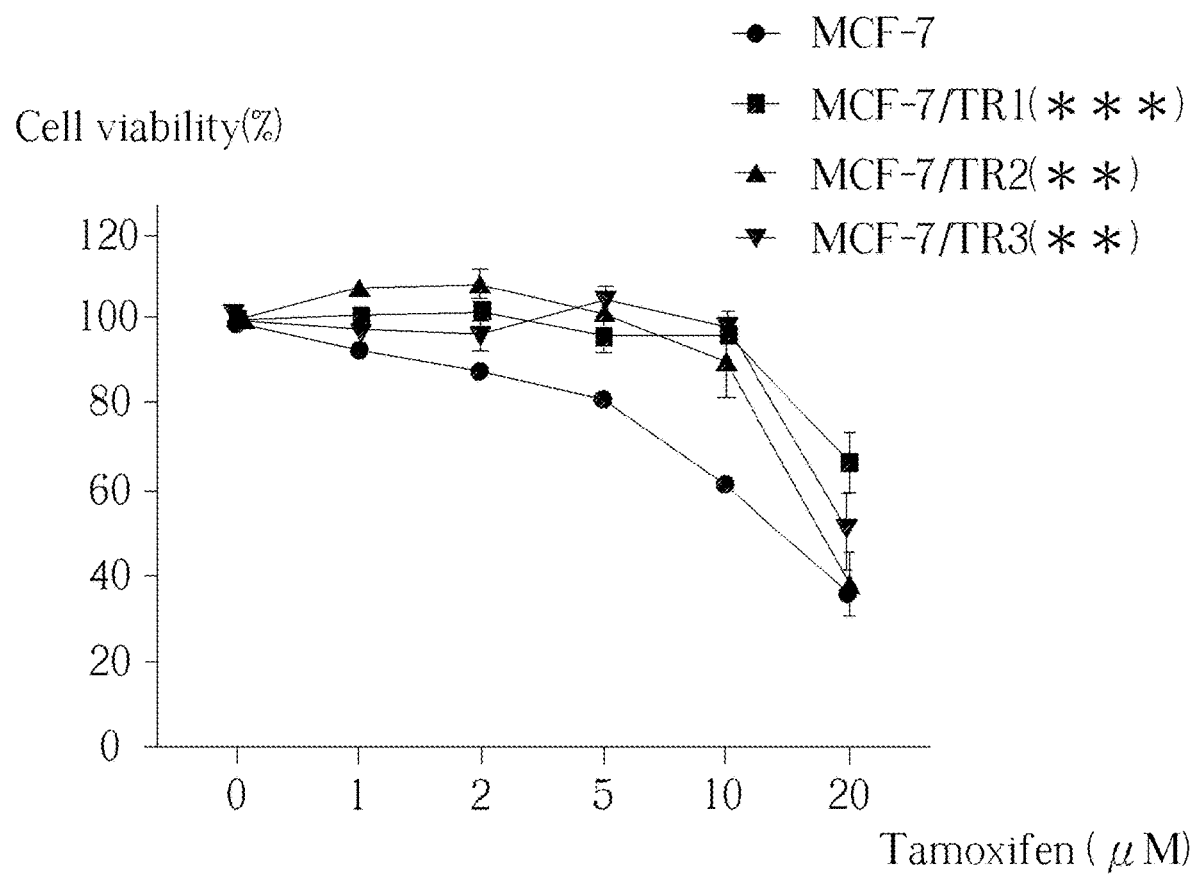
FIG. 2 is a schematic diagram illustrating establishment of tamoxifen-resistant cells according to the present invention.
Figure 3A:
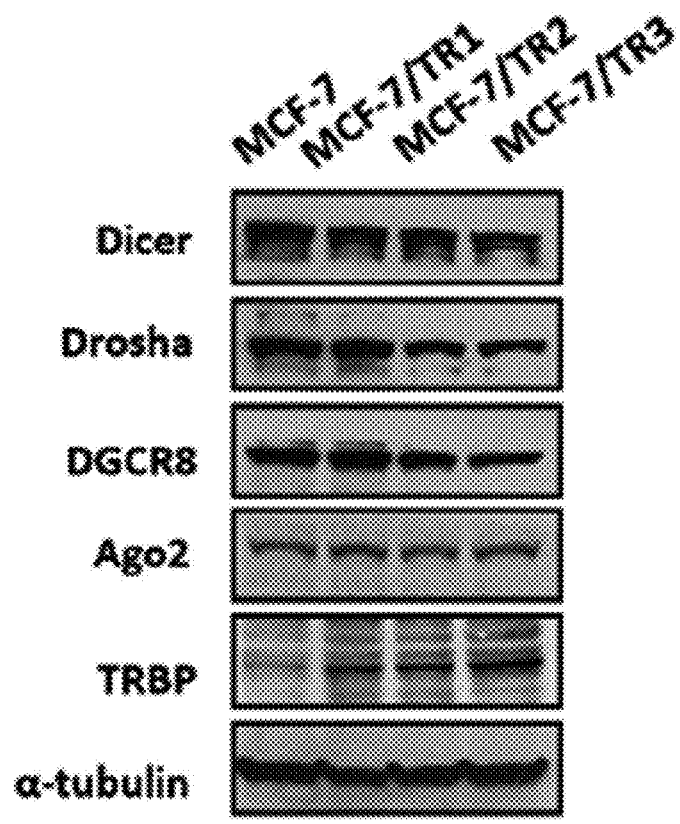

To determine the expression level of TRBP, we established tamoxifen-resistant cells including MCF-7/TR1, MCF-7/TR2 and MCF-7/TR3, and the resistance of the cells MCF-7/TR1, MCF-7/TR2 and MCF-7/TR3 were confirmed as shown in FIG. 2, in which, a tamoxifen-sensitive cell MCF-7 and the tamoxifen-resistant cells (MCF-7/TR1, MCF-7/TR2 and MCF-7/TR3) were treated with different concentrations of tamoxifen (such as 1, 2, 5, 10, 20 µM) for 72 hours and then the cell proliferations thereof are determined by using a MTT assay. Then, the expressions of different microRNA biogenesis factors in the tamoxifen-sensitive cell (MCF-7) and the tamoxifen-resistant cells (MCF-7/TR1, MCF-7/TR2 and MCF-7/TR3) were screened by seeding those cells in plates until those cells reached 70-80% confluence, followed by collecting and analyzing those cells respectively through a western blot, and we found that only TRBP expression was upregulated in the tamoxifen-resistant cells (MCF-7/TR1, MCF-7/TR2 and MCF-7/TR3), as shown in FIG. 3A.

Figure 3B:
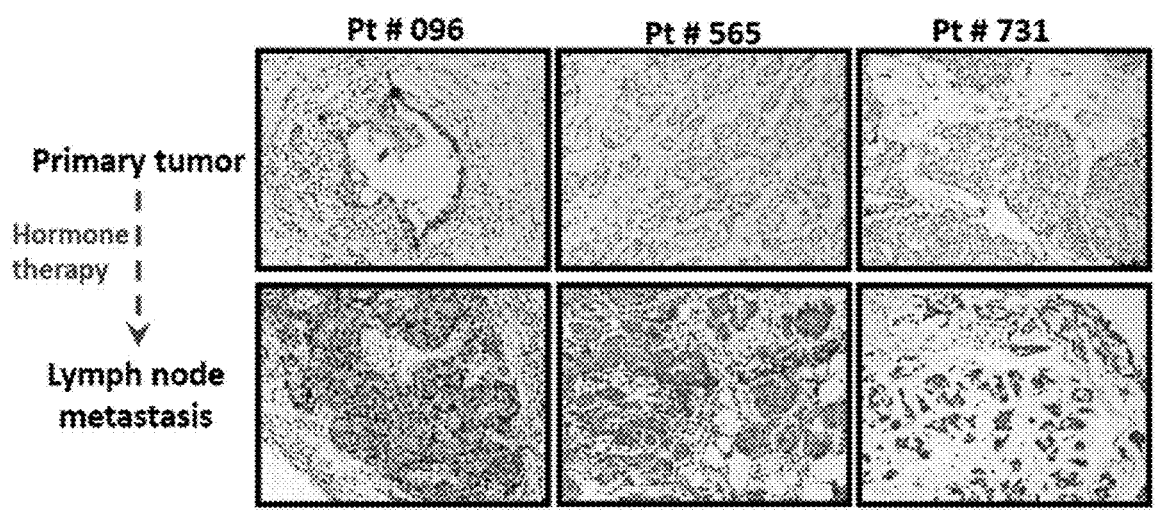
Figures 3C, 3D:
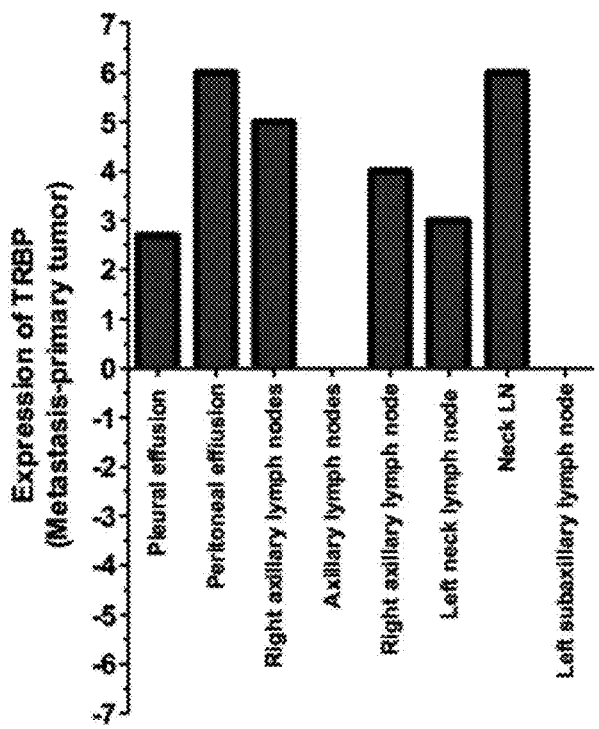

To establish whether the upregulation of TRBP in tamoxifen-resistant breast cancer cells could be observed in human tumors, we collected metastatic tumors and their corresponding primary tumors from breast cancer patients receiving hormone therapy and analyzed TRBP expression in these tissues by IHC, with data being shown in FIGS. 3B and 3D. As shown in FIG. 3C, TRBP was highly expressed in tumor cells in metastatic lymph nodes or pleural effusions compared with paired primary tumors from the same patient, and also, in seven paired tissues, a higher level of TRBP protein was observed in five metastatic sites from breast cancer patients.

Figure 3E:
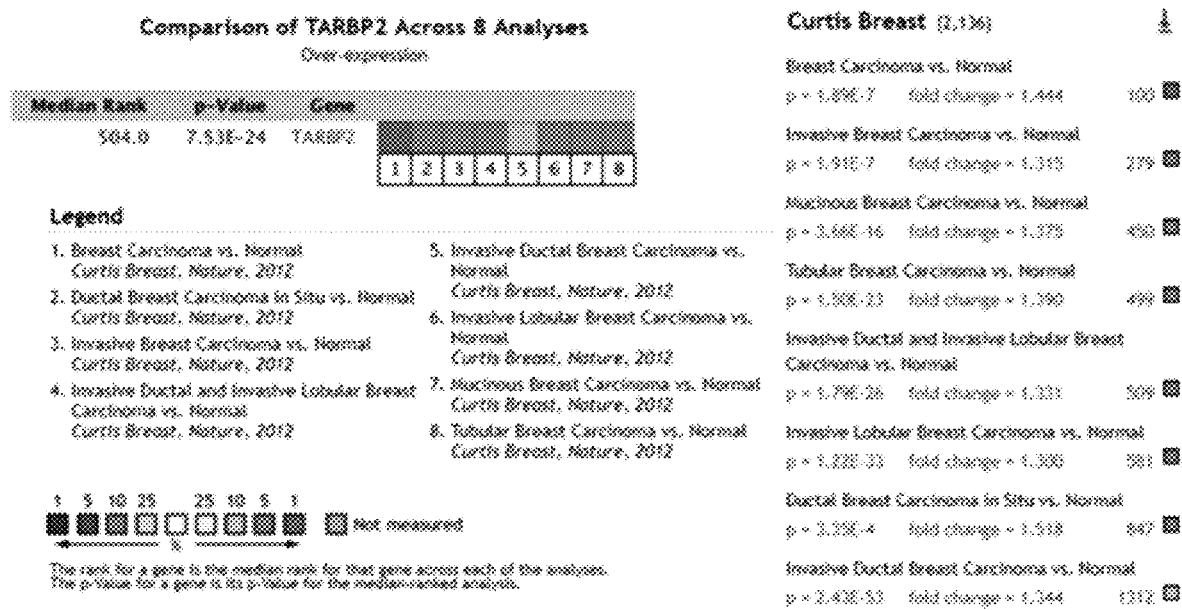
Figure 3F:
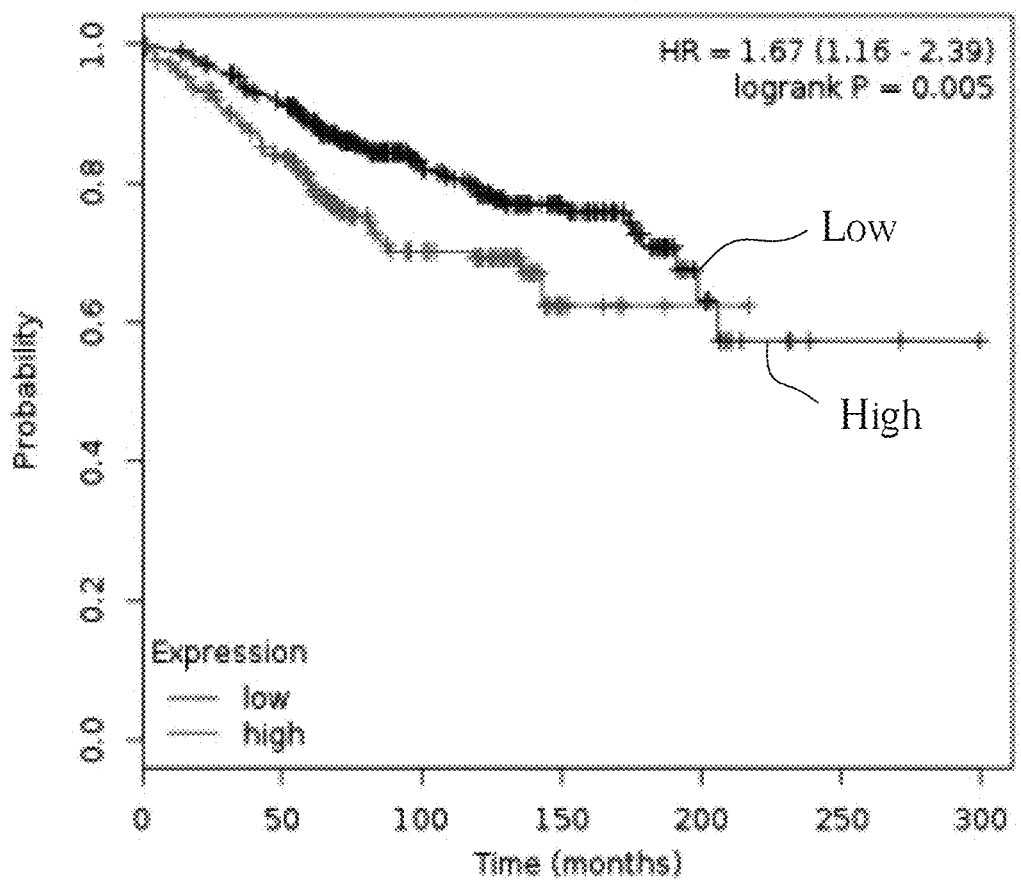
Figure 3G:
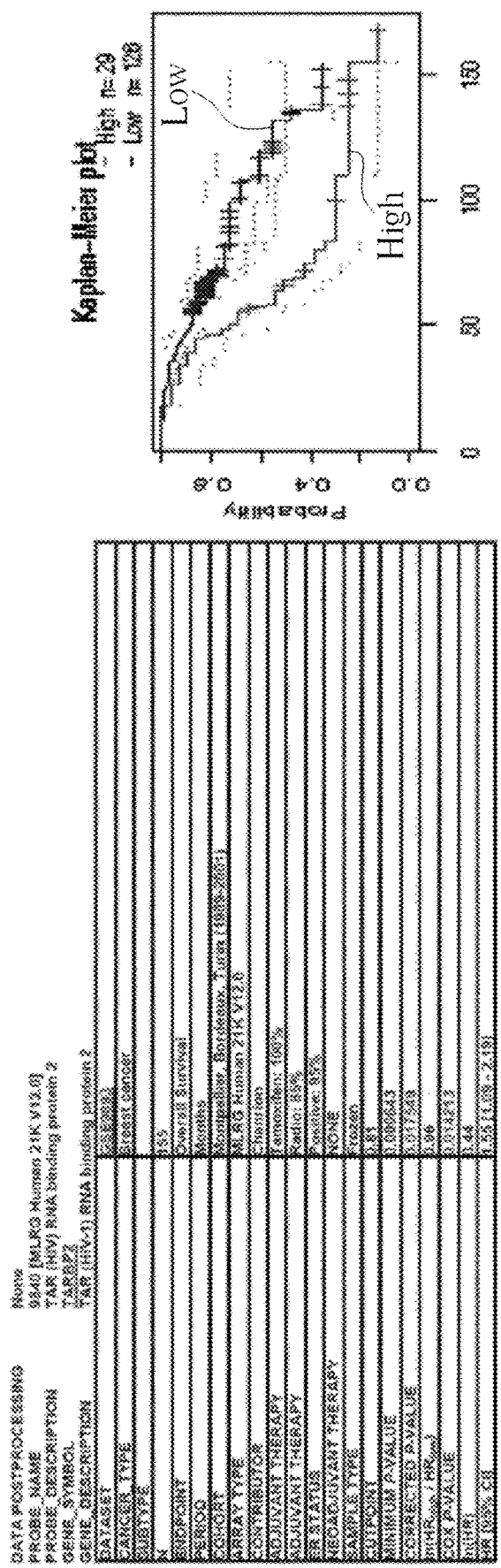

On the other hand, we also found that TRBP expression was significantly upregulated in breast cancer as compared with normal tissues in all datasets (18/18; 100%) in the Oncomine database, as shown in FIG. 3D. Furthermore, as shown in FIG. 3E, elevated TRBP level was observed in different subtypes of breast cancer. Also, in ER+ patients (as shown in FIG. 3F) and ER+ patients treated with adjuvant tamoxifen therapy (as shown in FIG. 3G), higher TRBP expression was observed to be significantly correlated with poor prognosis. Thus, the above results indicated that an elevated TRBP level is correlated with poor prognosis of ER+ patients and is associated with enhanced tamoxifen resistance.

II. Elevated TRBP Promotes Acquired Resistance to Tamoxifen.

Figure 4A:
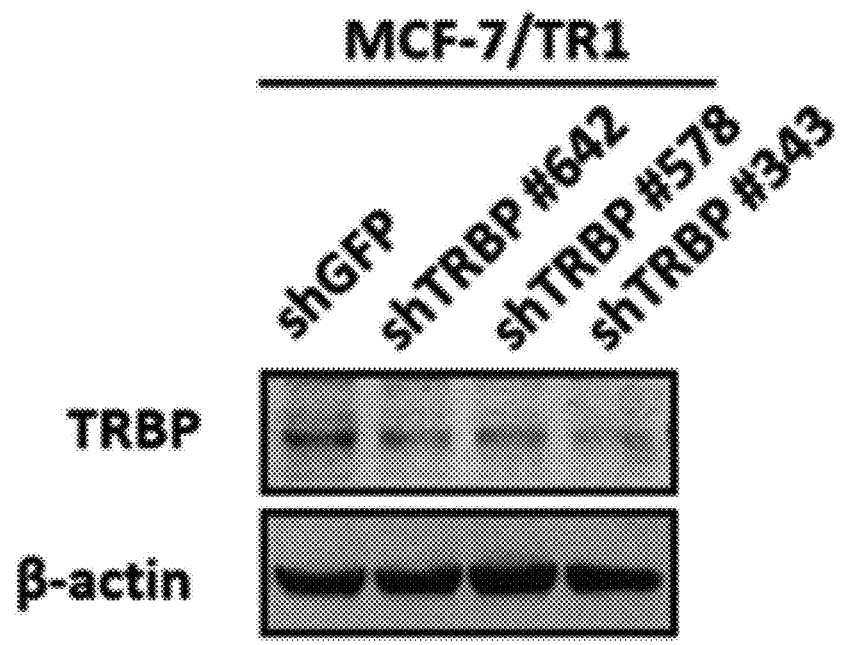
Figure 4B:
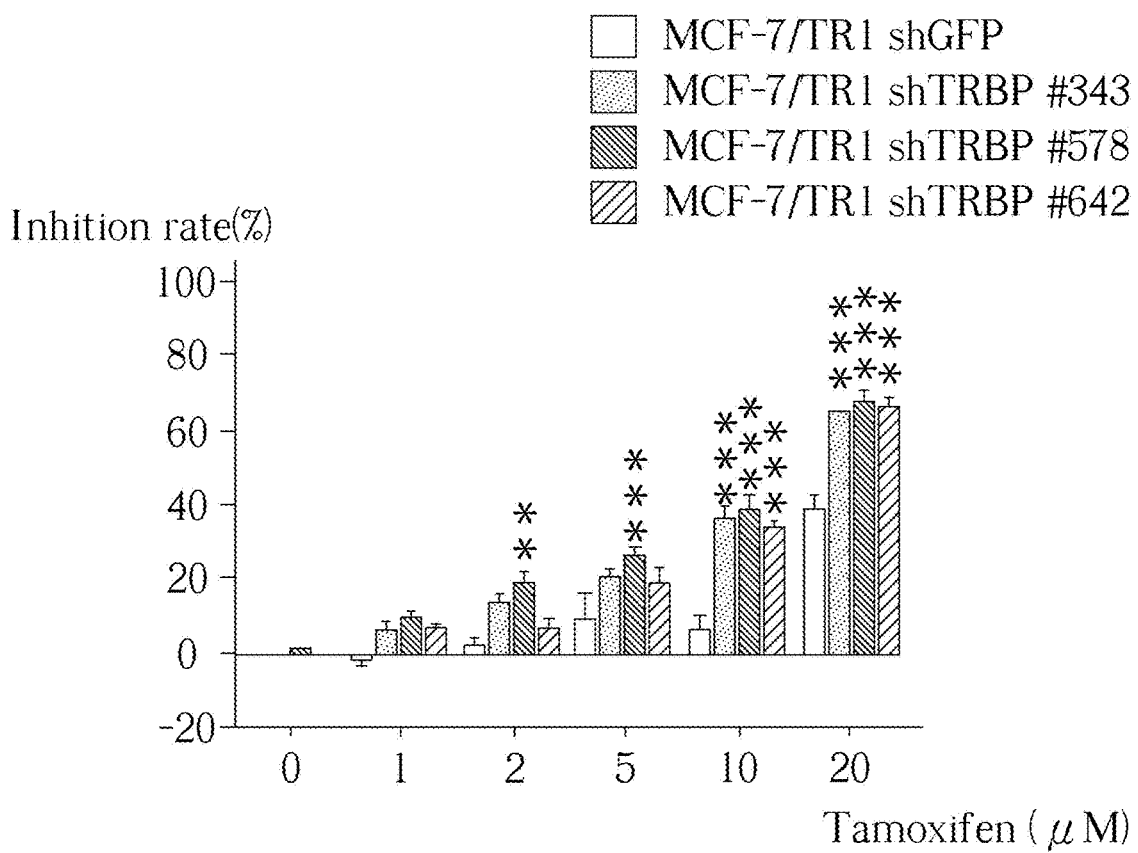
Figure 4C:
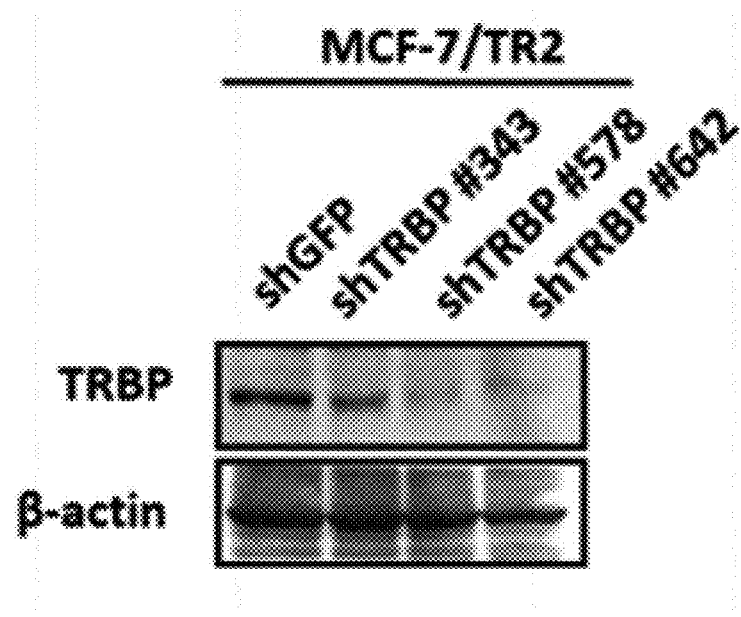
Figure 4D:
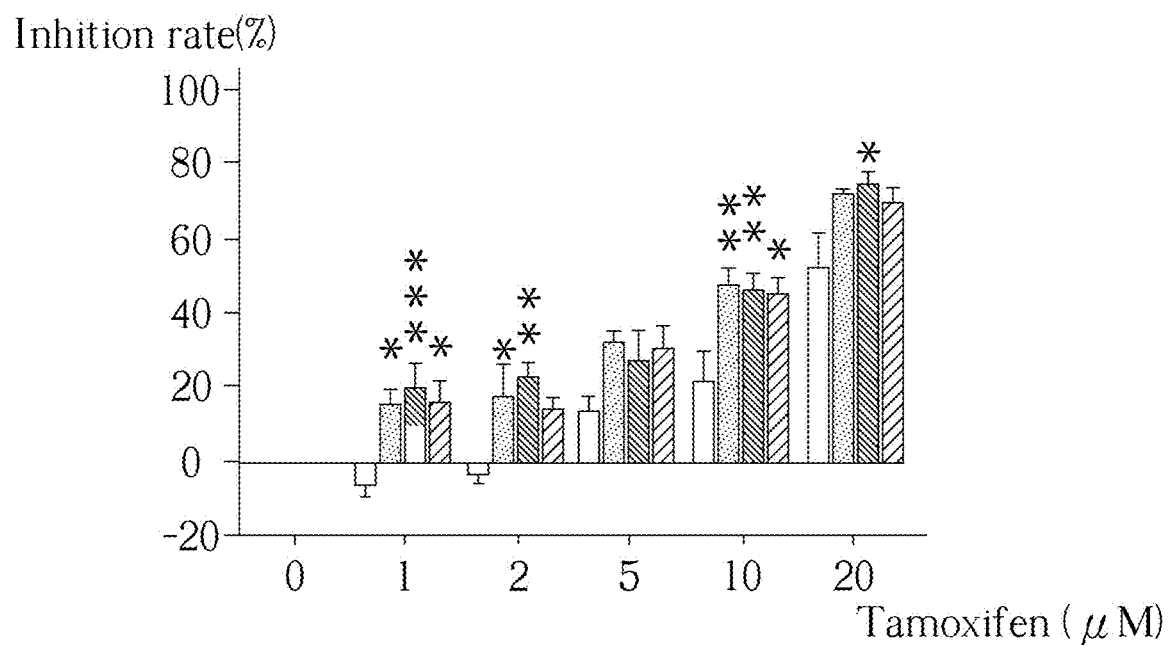
Figure 4E:
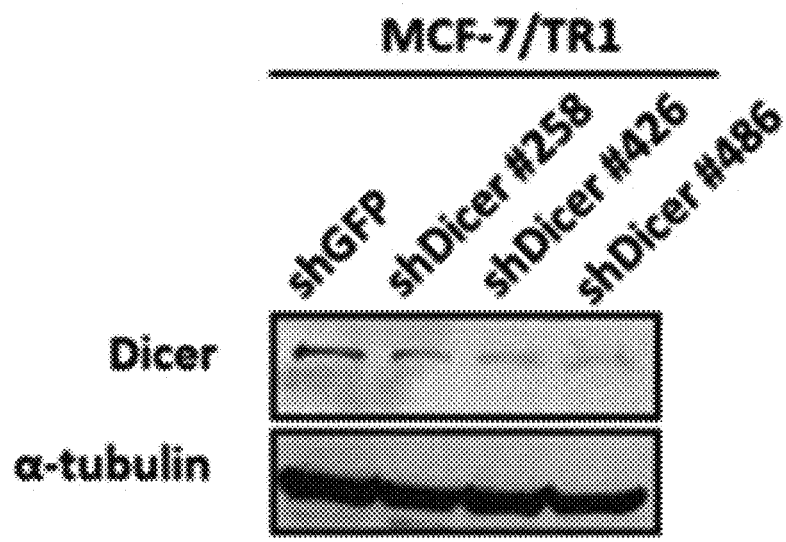
Figure 4F:
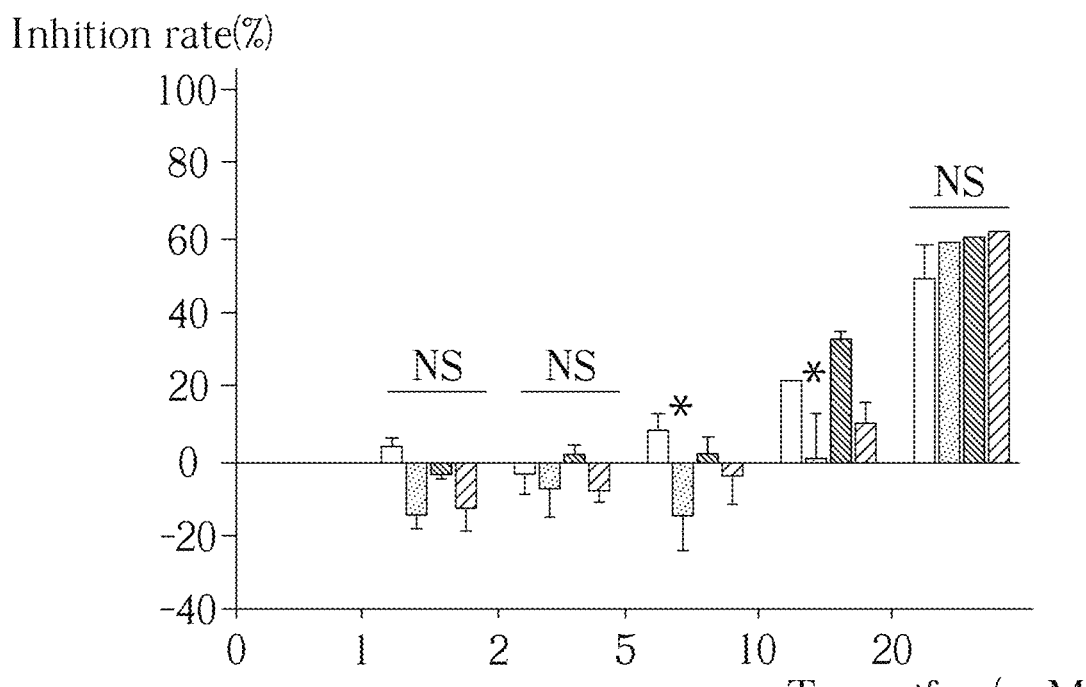
Figure 4G:
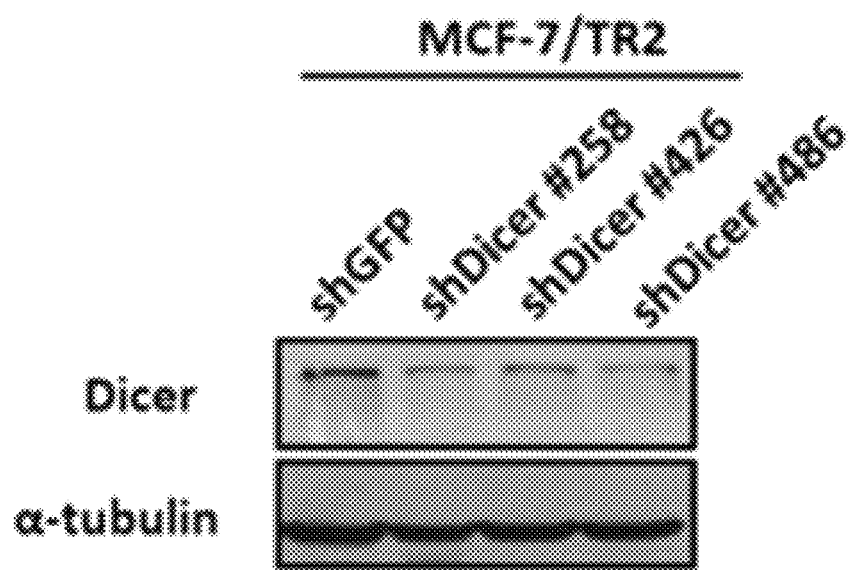
Figure 4H:
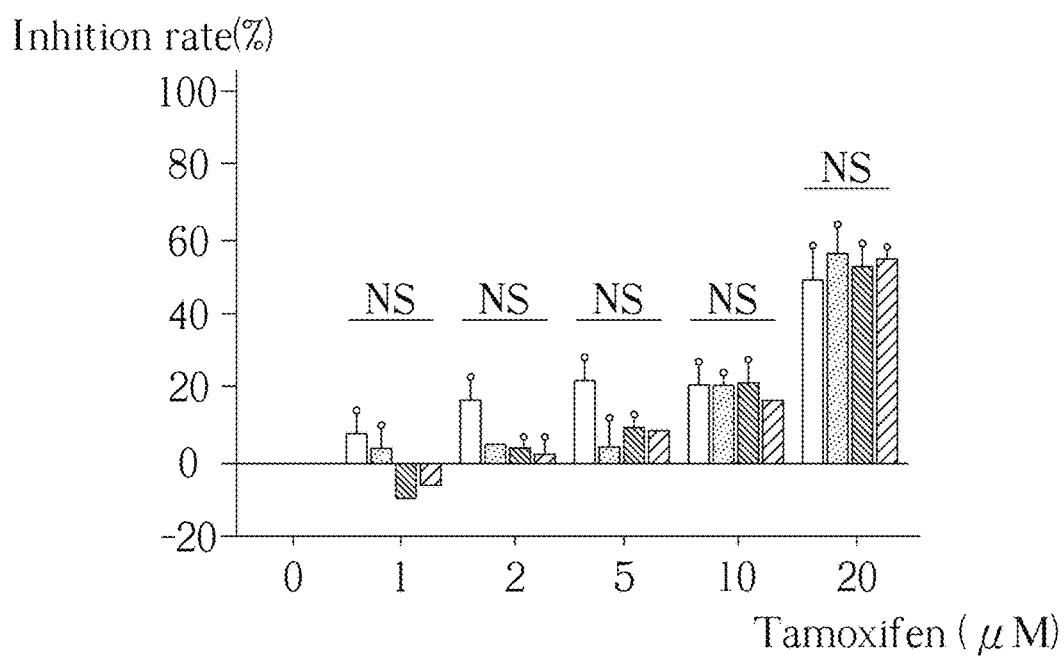

To investigate the potential role of TRBP in the modulation of tamoxifen resistance, we knocked down TRBP in the tamoxifen-resistant cells (MCF-7/TR1 and MCF-7/TR2) through administrating three specific shRNAs including shTRBP #642, shTRBP #578 and shTRBP #343. Precisely, the tamoxifen-resistant cells (MCF-7/TR1 and MCF-7/TR2) were transfected with the three shRNAs (shTRBP #642, shTRBP #578 and shTRBP #343) respectively for 48 hours, and the efficiency of TRBP knock-down in the tamoxifen-resistant cells was examined by another western blot, as shown in FIGS. 4A and 4C. Then, the tamoxifen-resistant cells (MCF-7/TR1 and MCF-7/TR2) were treated with different doses of tamoxifen (such as 1, 2, 5, 10, 20 µM) for 72 hours, and cell proliferations of the tamoxifen-resistant cells (MCF-7/TR1 and MCF-7/TR2) were subjected to another MTT assay respectively, to evaluate drug sensitivities thereof, with data thereof being shown in FIGS. 4B and 4D. As shown in FIGS. 4B and 4D, the depletion of TRBP significantly enhanced tamoxifen sensitivity of the tamoxifen-resistant cells (MCF-7/TR1 and MCF-7/TR2), which indicated that TRBP upregulation is essential for acquired tamoxifen resistance. Furthermore, through similar process of knocked down TRBP, we also knocked down Dicer in the tamoxifen-resistant cells (MCF-7/TR1 and MCF-7/TR2) as shown in FIGS. 4E and 4G, to investigate whether tamoxifen resistance relies on its function in miRNA regulation, and however, the knockdown of Dicer did not affect the sensitivity of the tamoxifen-resistant cells (MCF-7/TR1 and MCF-7/TR2) to tamoxifen, as shown in FIGS. 4F and 4H.

Figure 4I:
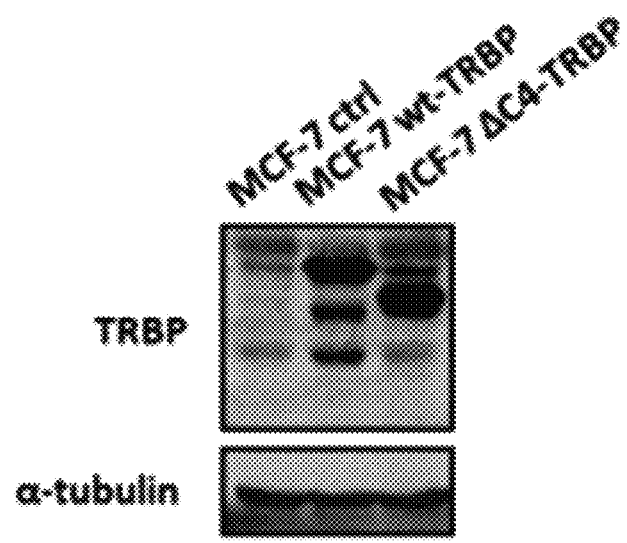
Figure 4J:
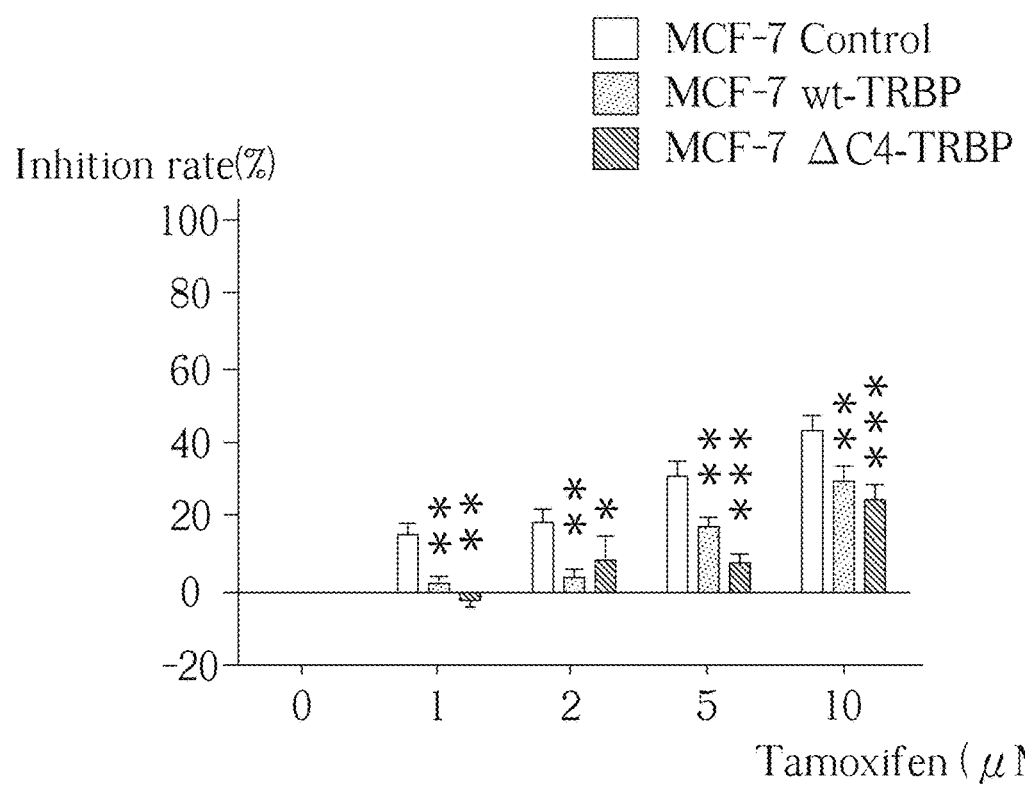

Moreover, we transfected the tamoxifen-sensitive cell (MCF-7) with a C4-truncated TRBP, which has lost its Dicer-binding domain, to further confirm whether TRBP-enhanced resistance acts through the miRNA pathway. Precisely, the tamoxifen-sensitive cells (MCF-7) were transfected with a control, wt-TRBP, or ΔC4-TRBP (namely the C4-truncated TRBP) plasmids respectively. After 24 hours of incubation, the tamoxifen-resistant cells (MCF-7/TR1 and MCF-7/TR2) were harvested to determine the TRBP expression by another western blot. Then, the tamoxifen-resistant cells (MCF-7/TR1 and MCF-7/TR2) were further treated with different concentrations of tamoxifen (1, 2, 5, 10, 20 µM) for 72 hours, followed by using another MTT assay to evaluate cell viabilities thereof, wherein all MTT results are presented as the means±SEM from at least three separate experiments that were performed in duplicate or triplicate and analyzed by two-way ANOVA (*P≤0.05, P≤0.01, *P≤0.001). Consistently, as shown in FIGS. 4I and 4J, enhanced tamoxifen resistance was observed in MCF-7 cells after TRBP overexpression, and the promoting effects were also observed in cells that overexpressed C4-truncated TRBP. Thus, the above results indicate that the upregulation of TRBP confers acquired resistance to tamoxifen in breast cancer cells.

III. Tamoxifen-Induced TRBP Results in the Desensitization of ER+ Breast Cancer Cells.

Our previous results showed that TRBP is upregulated in tamoxifen-resistant breast cancer cells and tumors, so that it is believed TRBP contributes to an acquire resistance to tamoxifen. However, drug resistance may arise from the changes in expression that are observed in resistant cells during the selection process and the expansion of cells that survived. In the present experiment, the TRBP upregulation was observed only in a tamoxifen-resistant cell (MCF-7/TR) which is selected over the long term using tamoxifen in the present experiment, in which, the tamoxifen-resistant cell (MCF-7/TR) and an ER+ breast cancer cell (ZR-75-1) were prepared and treated with increasing concentrations of tamoxifen or 4-hydroxytamoxifen (4OHT) respectively, for 48 hours, and another western blot was performed to examine the TRBP expression therein, and cytotoxic effects of the indicated concentrations within the aforementioned cells were evaluated by another MTT assay, with all MTT results being presented as the means±SEM from at least three separate experiments that were performed in duplicate or triplicate.

Figure 5A:
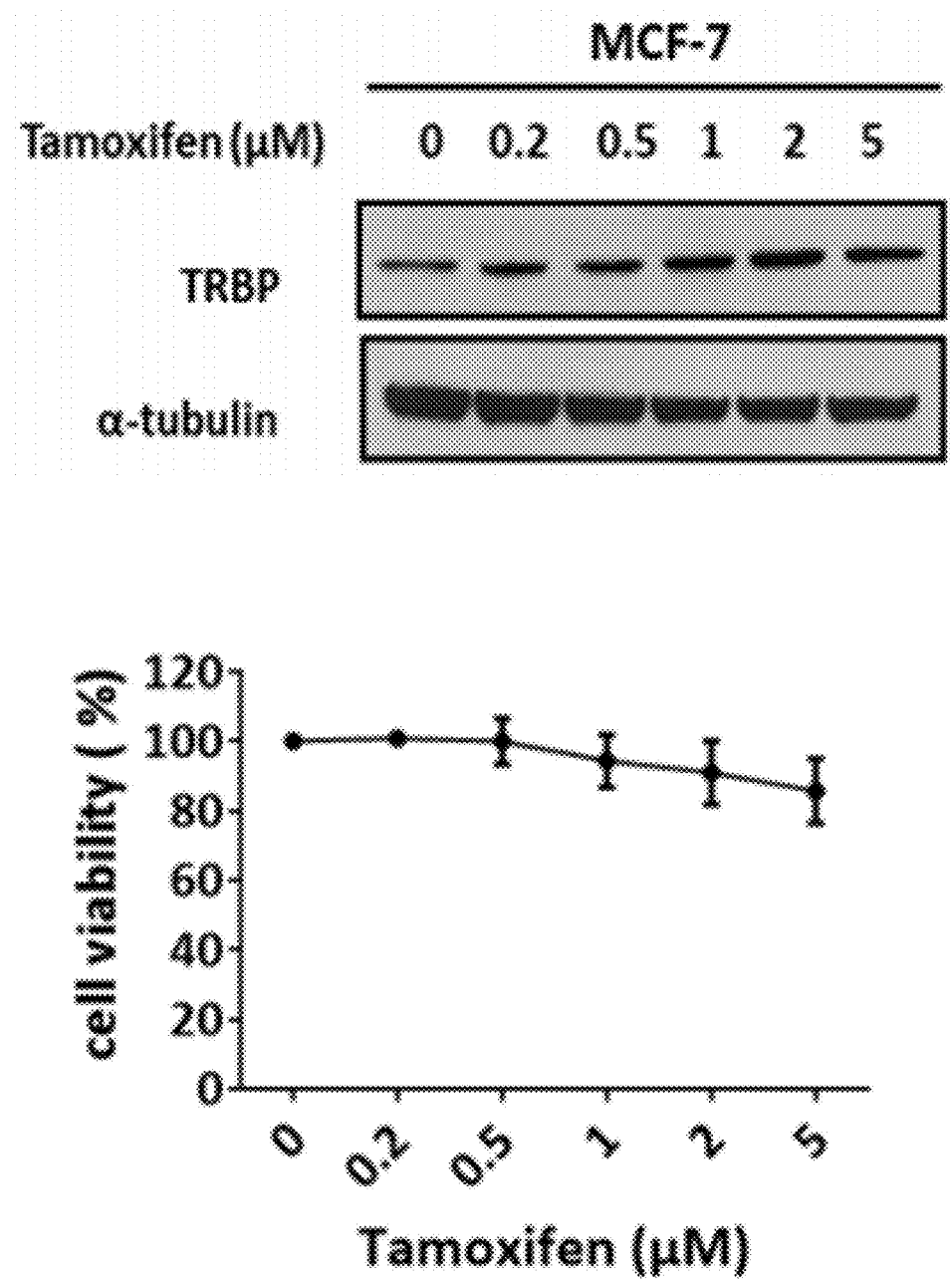
Figure 5B:
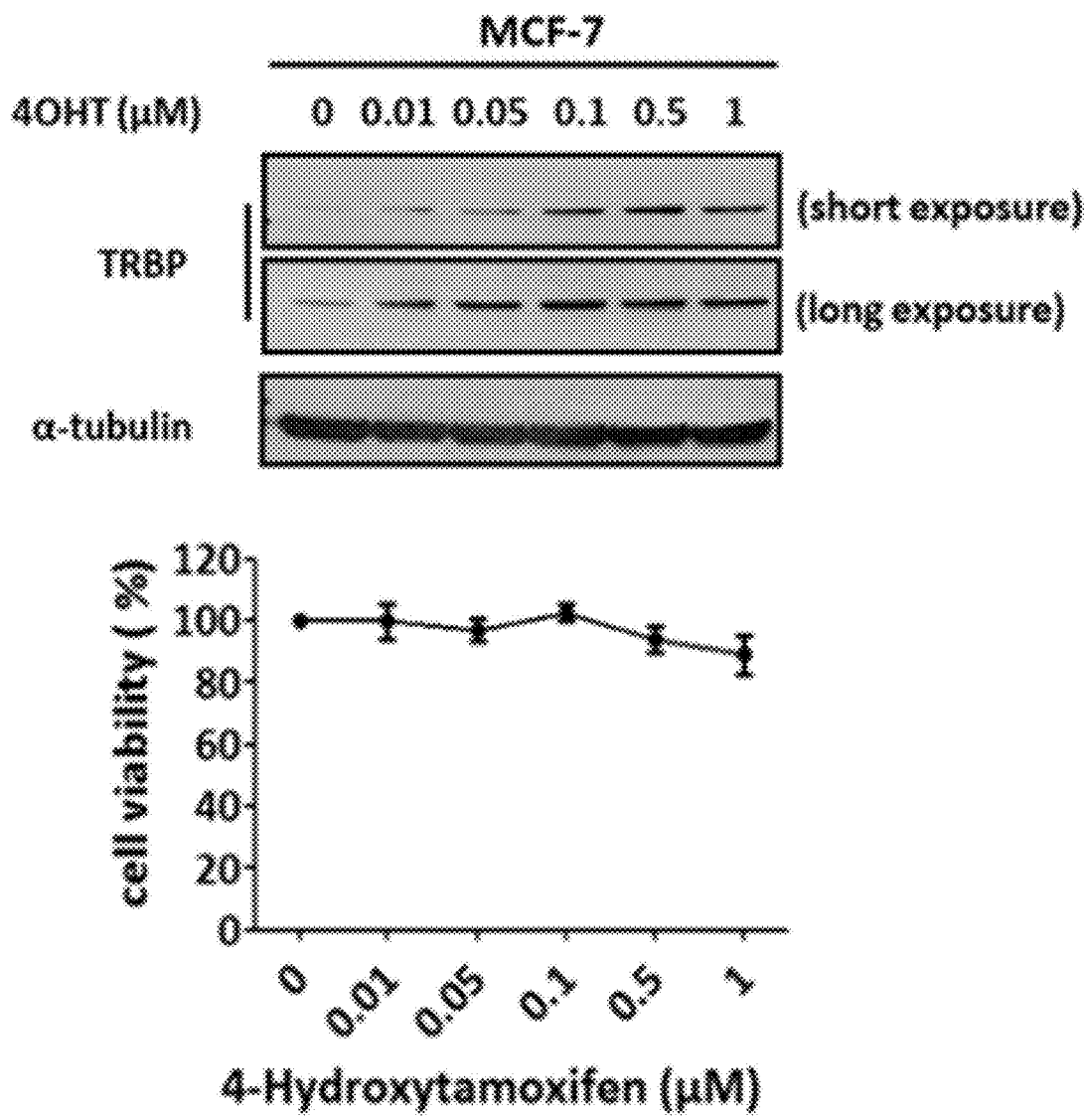
Figure 5C:
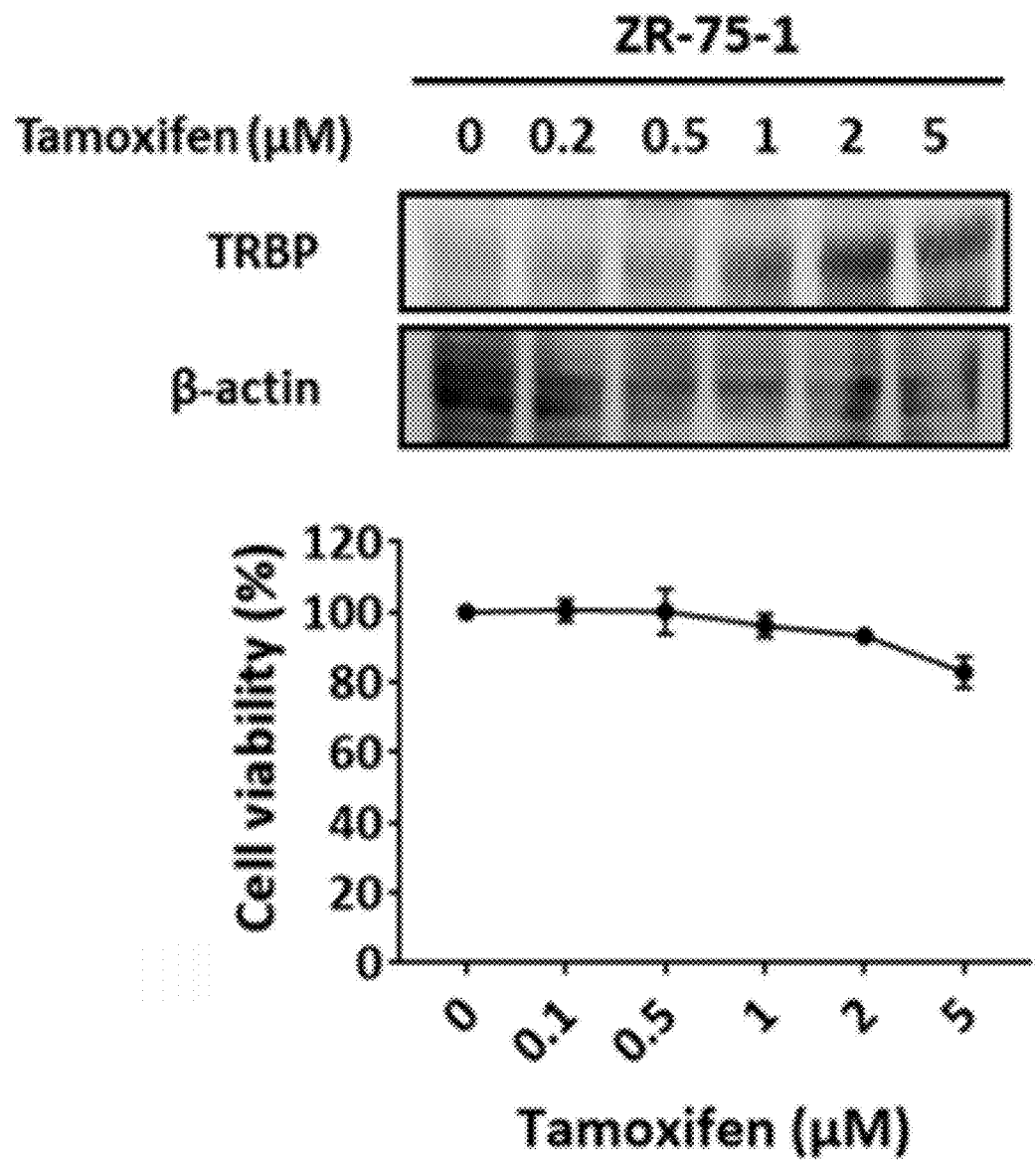
Figure 5D:
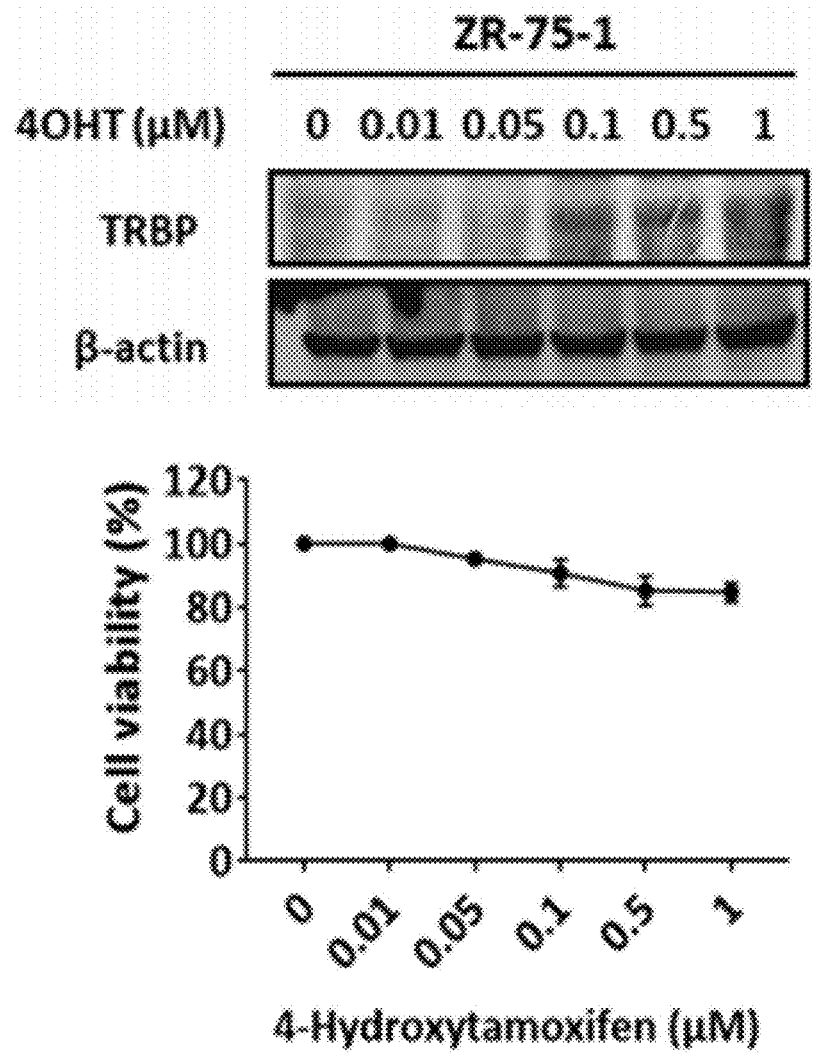
Figure 5E:
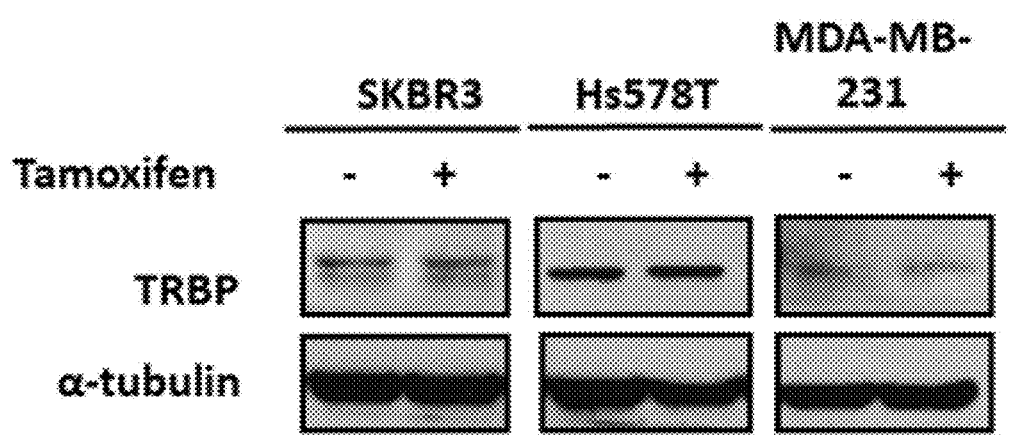

It is noted that, we observed that the treatment of the tamoxifen-resistant cell (MCF-7/TR) with tamoxifen also induced the TRBP expression in a dose-dependent manner as shown in left of FIG. 5A without inducing any significant cytotoxic effects as shown in right of FIG. 5A. Also, similar phenomena were also observed in the tamoxifen-resistant cell (MCF-7/TR) treated with 4-Hydroxytamoxifen (namely a metabolically active form of tamoxifen) which is found in the human body, with data thereof being shown in FIG. 5B. Furthermore, the ER+ breast cancer cell (ZR-75-1) treated with tamoxifen or 4-OHT also observes similar dose-dependent effects on the induction of TRBP expression under short-term and noncytotoxic treatments, as shown in FIGS. 5C and 5D. In contrast, no significant induction of TRBP was found in ER negative (ER−) breast cancer cells including SKBR3, Hs578T, and MDA-MB-231, as shown in FIG. 5E, while the ER− breast cancer cells (SKBR3, Hs578T, and MDA-MB-231) also treated with tamoxifen for 48 hours and analyzed the TRBP expressions therein by the western blot. Thus, the above results indicate that the induction of TRBP is driven by tamoxifen treatment in ER+ breast cancer cells. In other words, TRBP is upregulated and involved in the acquired resistance of the tamoxifen-resistant cell (MCF-7/TR).

Figure 6A:
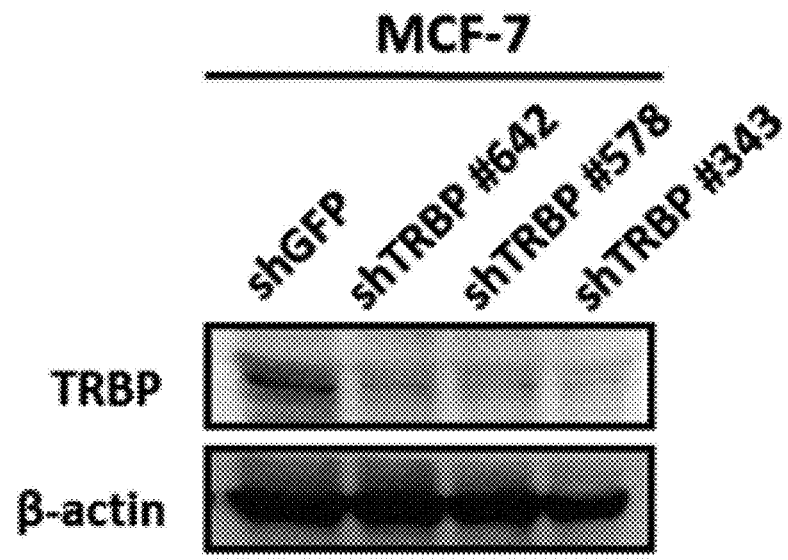
Figure 6B:
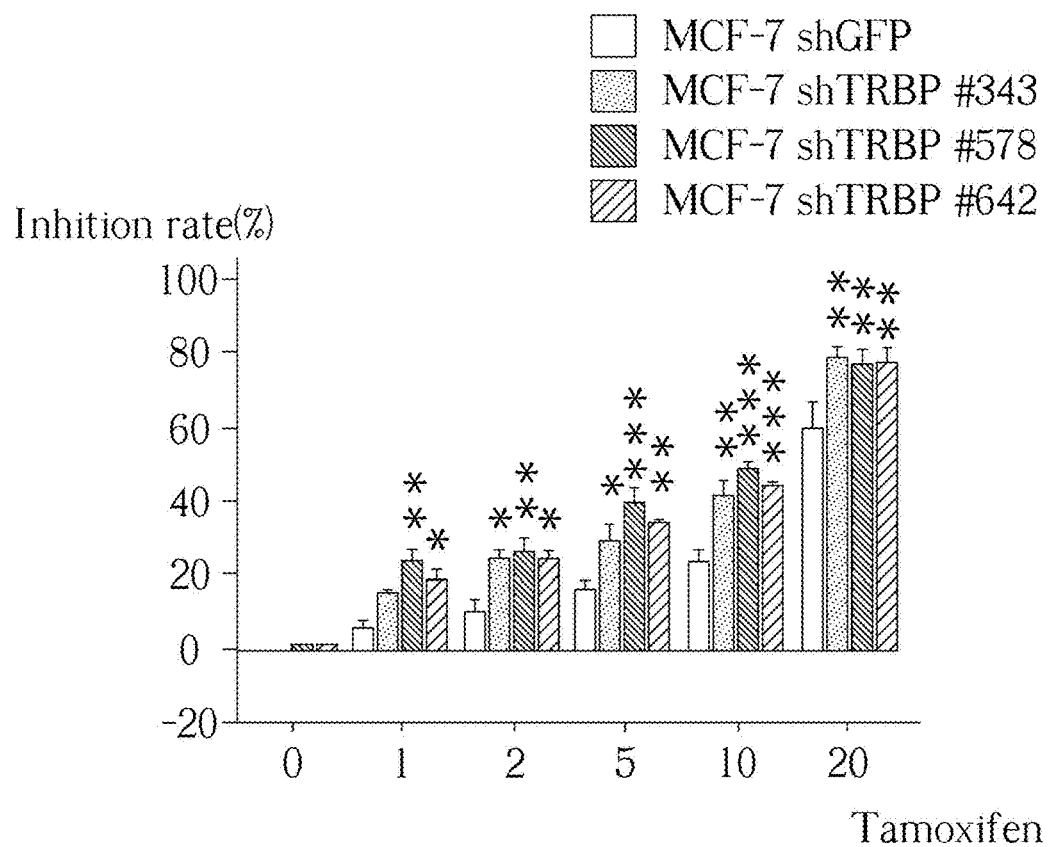
Figure 6C:
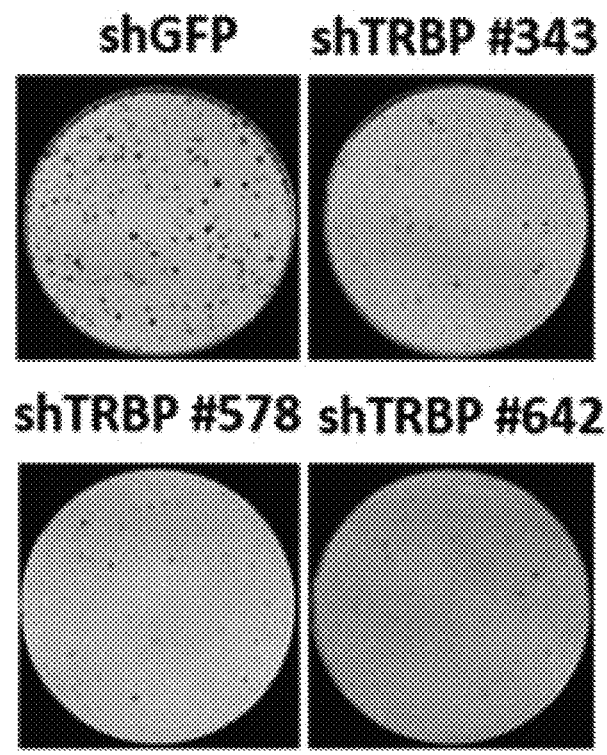
Figure 6C:
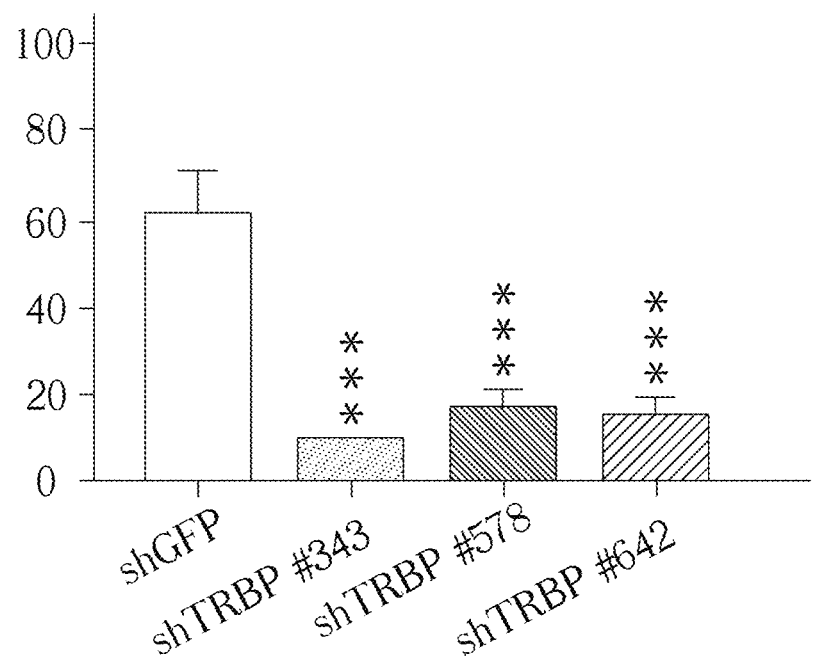
Figure 6D:
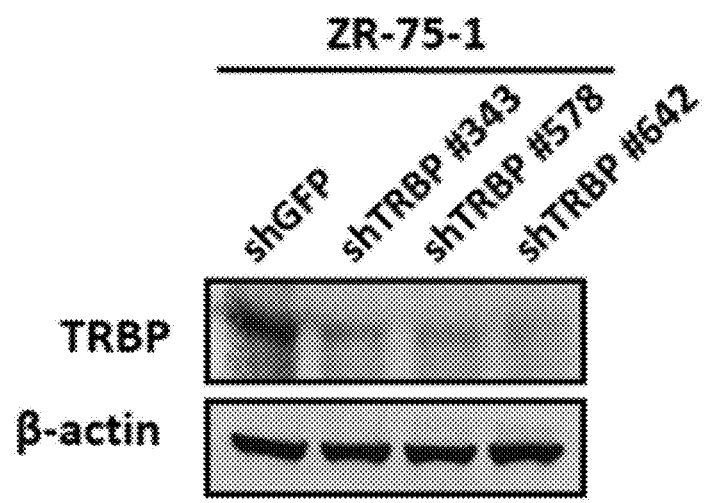
Figure 6E:
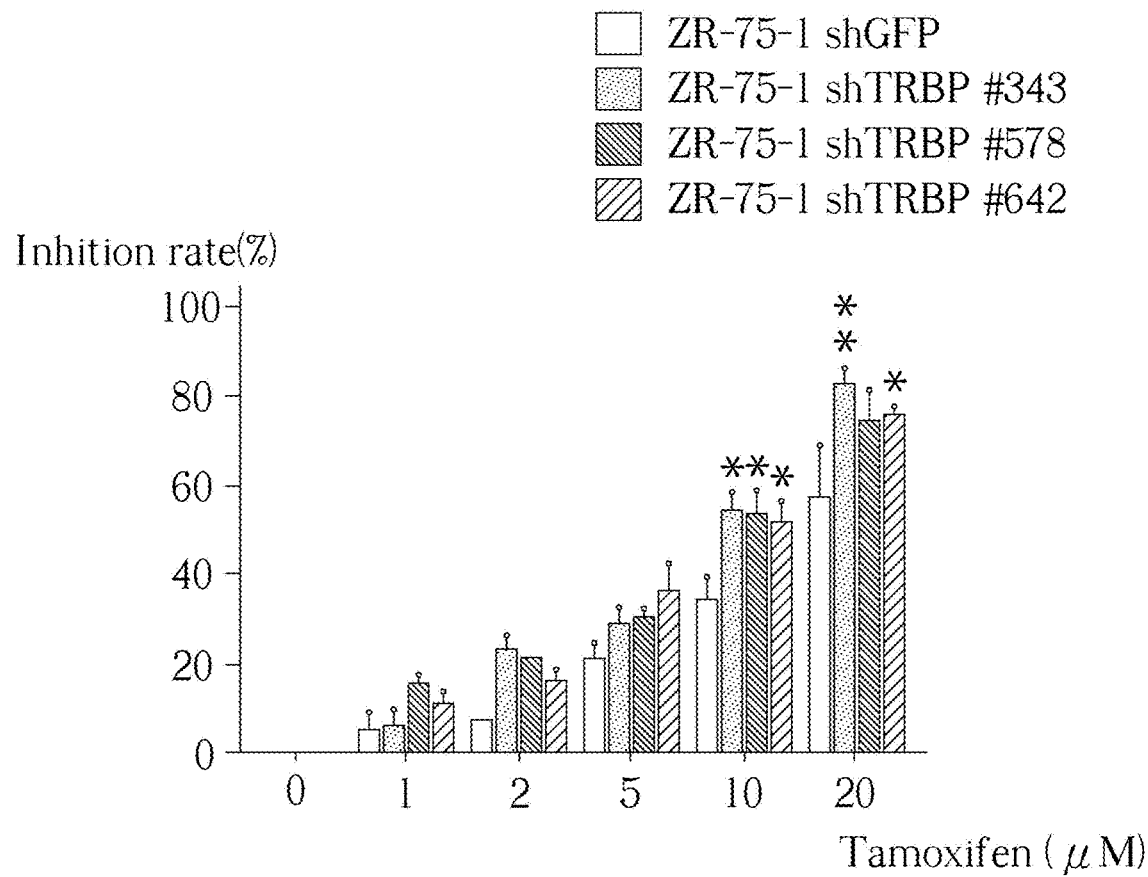
Figure 6F:
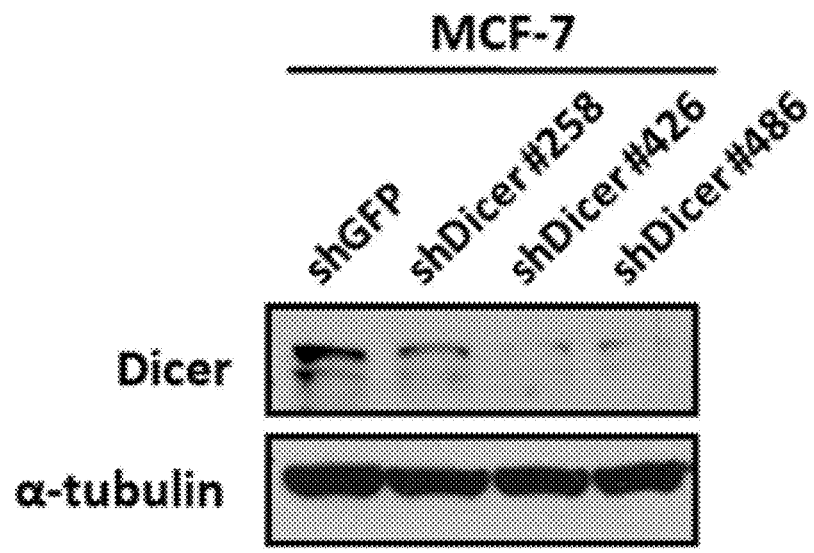
Figure 6G:
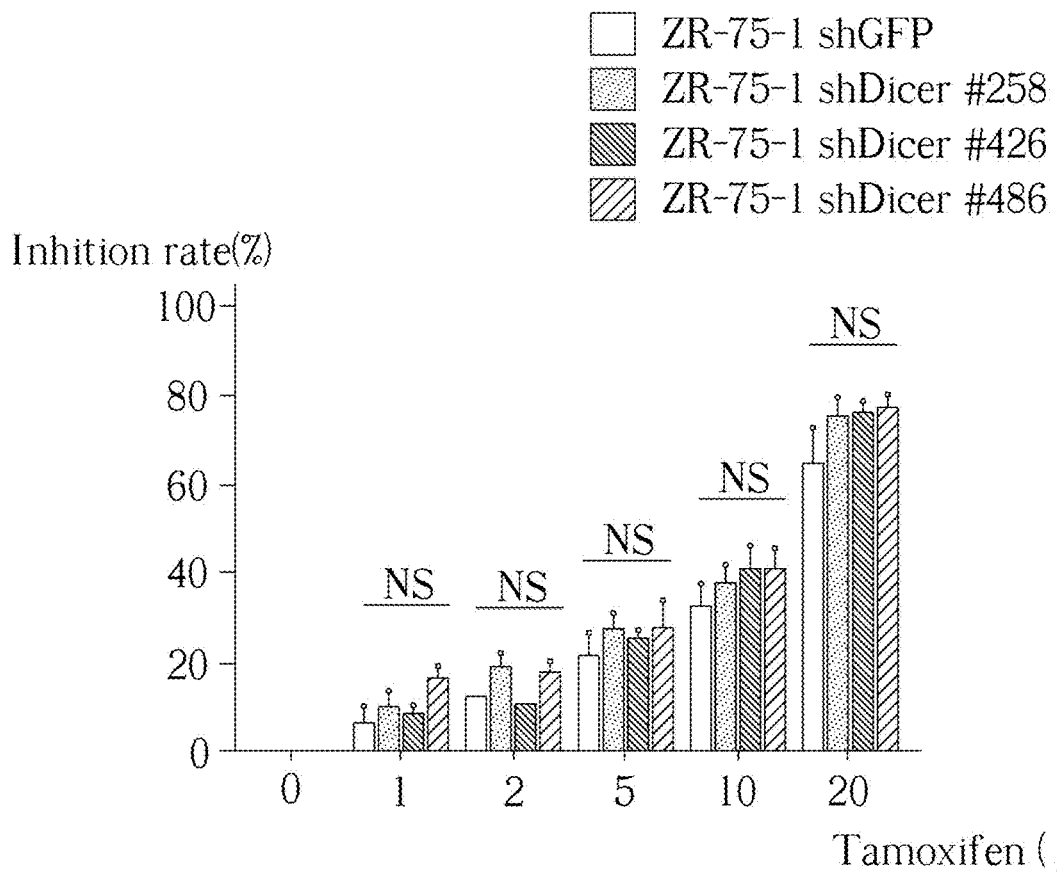
Figure 6H:
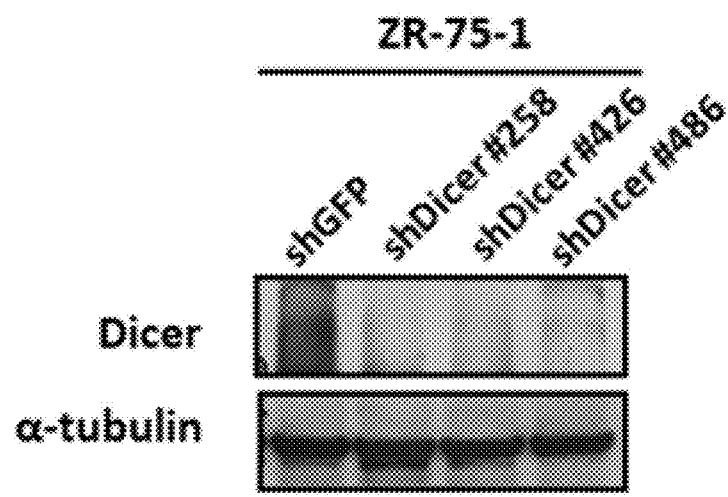
Figure 6I:
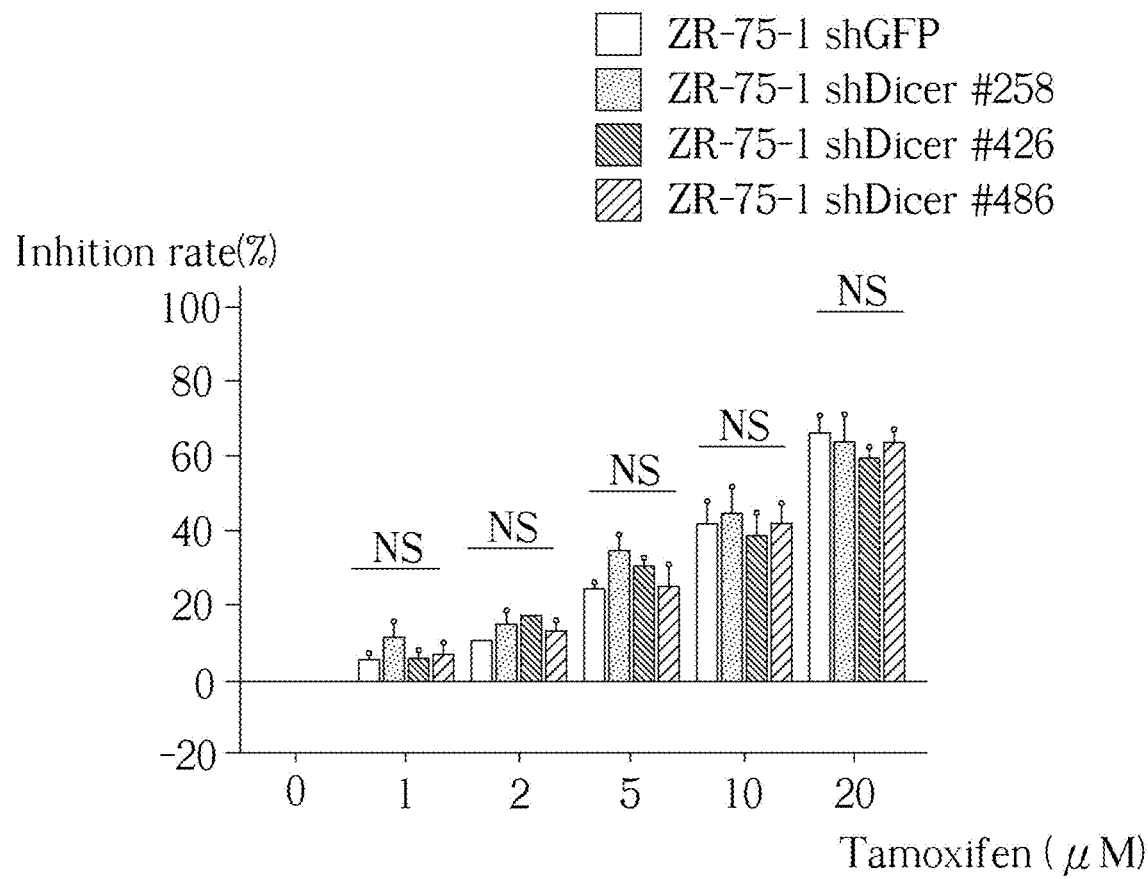

Next, to investigate the functional contribution of TRBP, we further used the shRNAs (shTRBP #642, shTRBP #578 and shTRBP #343) to block the tamoxifen-induced TRBP and to determine the viability of the tamoxifen-resistant cell (MCF-7/TR) in the presence of tamoxifen as shown in FIG. 6A, in which, the tamoxifen-resistant cell (MCF-7/TR) and the ER+ breast cancer cell (ZR-75-1) were transfected with shRNAs (shTRBP #642, shTRBP #578 and shTRBP #343) targeting TRBP for 48 hours, with efficiencies of TRBP knock-down thereof being examined by another western blot, and the tamoxifen-resistant cell (MCF-7/TR) and the ER+ breast cancer cell (ZR-75-1) transfected with the shRNAs (shTRBP #642, shTRBP #578 and shTRBP #343) were then treated with different concentrations of tamoxifen (1, 2, 5, 10, 20 µM) for 72 hours, with proliferations and colony-forming abilities of the tamoxifen-resistant cell (MCF-7/TR) and the ER+ breast cancer cell (ZR-75-1) being determined by another MTT assay (as shown in FIGS. 6B, 6E) and a colony formation assays (as shown in FIG. 6C). At different doses of tamoxifen treatment, TRBP in the tamoxifen-resistant cell (MCF-7/TR) was knocked down by the shRNAs (shTRBP #642, shTRBP #578 and shTRBP #343), so that, the tamoxifen-resistant cell (MCF-7/TR) therefore presents a higher tamoxifen sensitivity according to the MTT data as shown in FIG. 6B and the colony formation data as shown in FIG. 6C. Also, similar effects were also observed in the tamoxifen-treated ER+ breast cancer cell (ZR-75-1) as shown in FIGS. 6D and 6E, while TRBP in the ER+ breast cancer cell (ZR-75-1) was knocked down by the shRNAs (shTRBP #642, shTRBP #578 and shTRBP #343). Thus, the above evidences suggest that the upregulation of TRBP is directly triggered by tamoxifen and consequently results in enhanced primary tamoxifen resistance. Again, the knockdown of Dicer in the tamoxifen-treated tamoxifen-resistant cell (MCF-7/TR) and the tamoxifen-treated ER+ breast cancer cell (ZR-75-1) did not affect drug sensitivity as shown in FIGS. 6F, 6G and 6I, which supports the concept that tamoxifen induced TRBP enhances drug resistance in a miRNA-independent manner.

IV. Tamoxifen Posttranscriptionally Stabilizes TRBP Protein Expression Through Downregulation of Merlin.

Figure 7A:
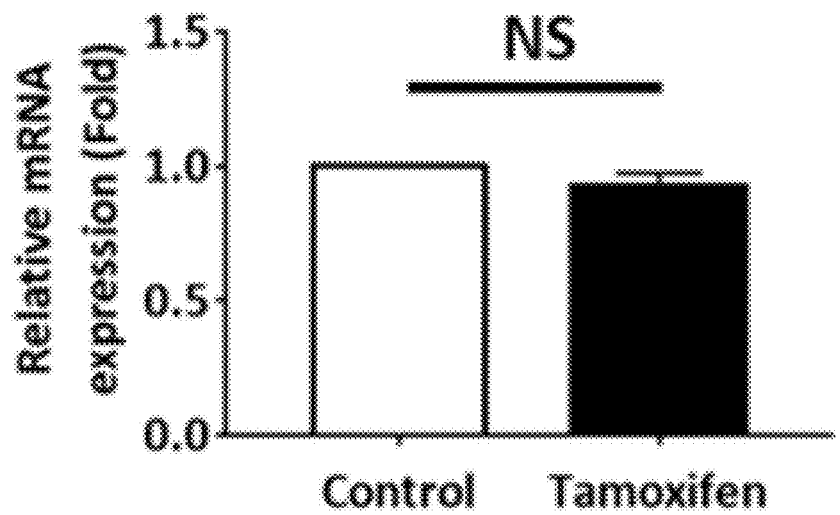
Figure 7A:
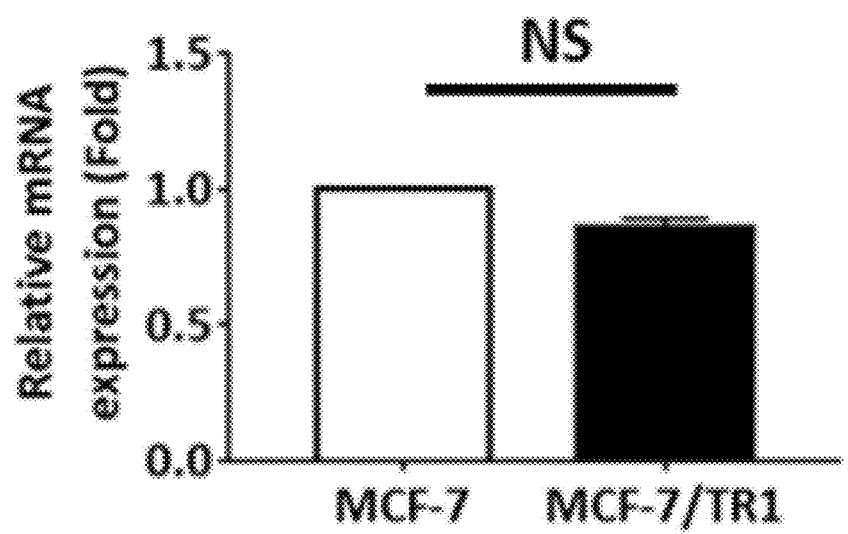
Figure 7B:
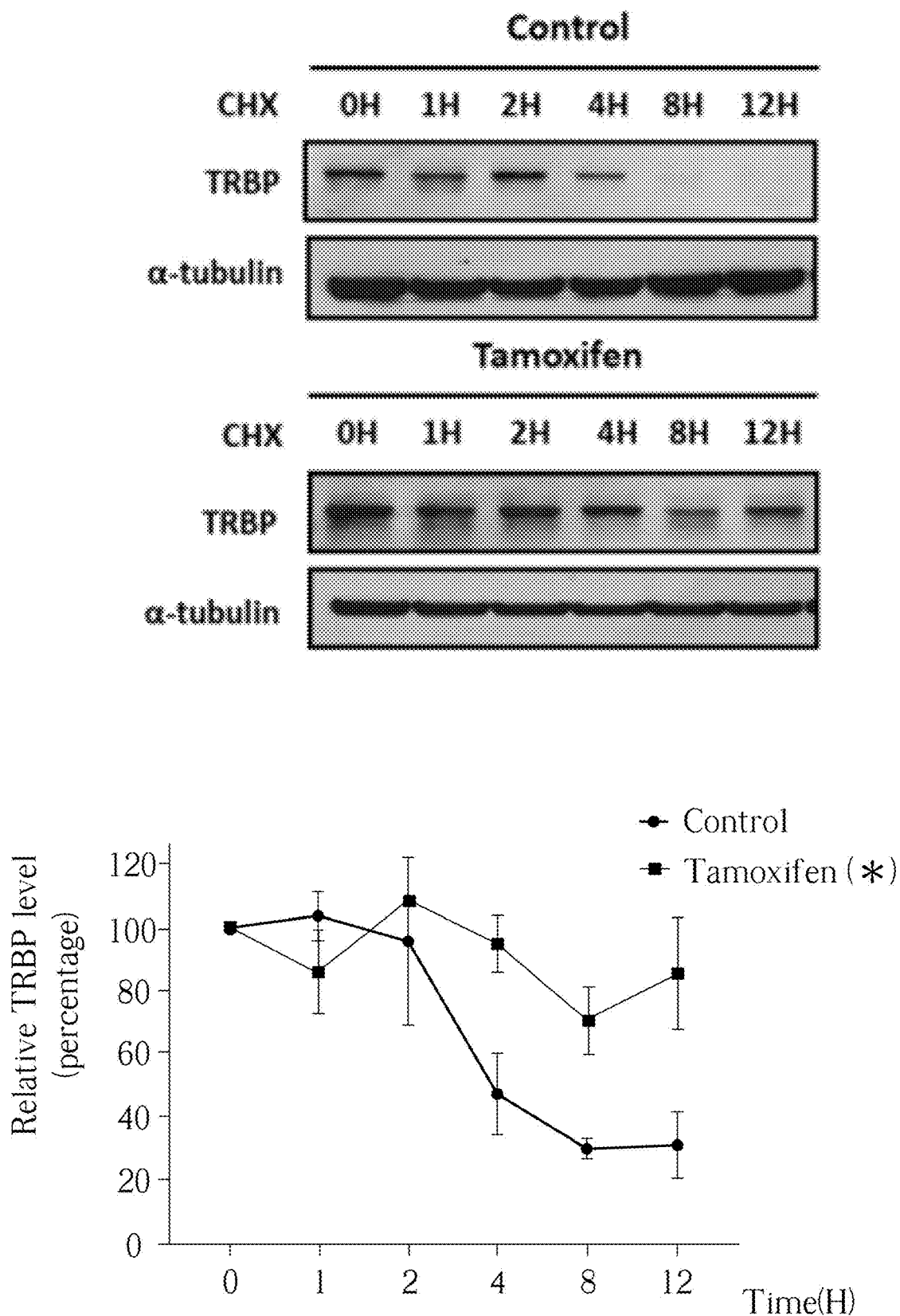
Figure 7C:
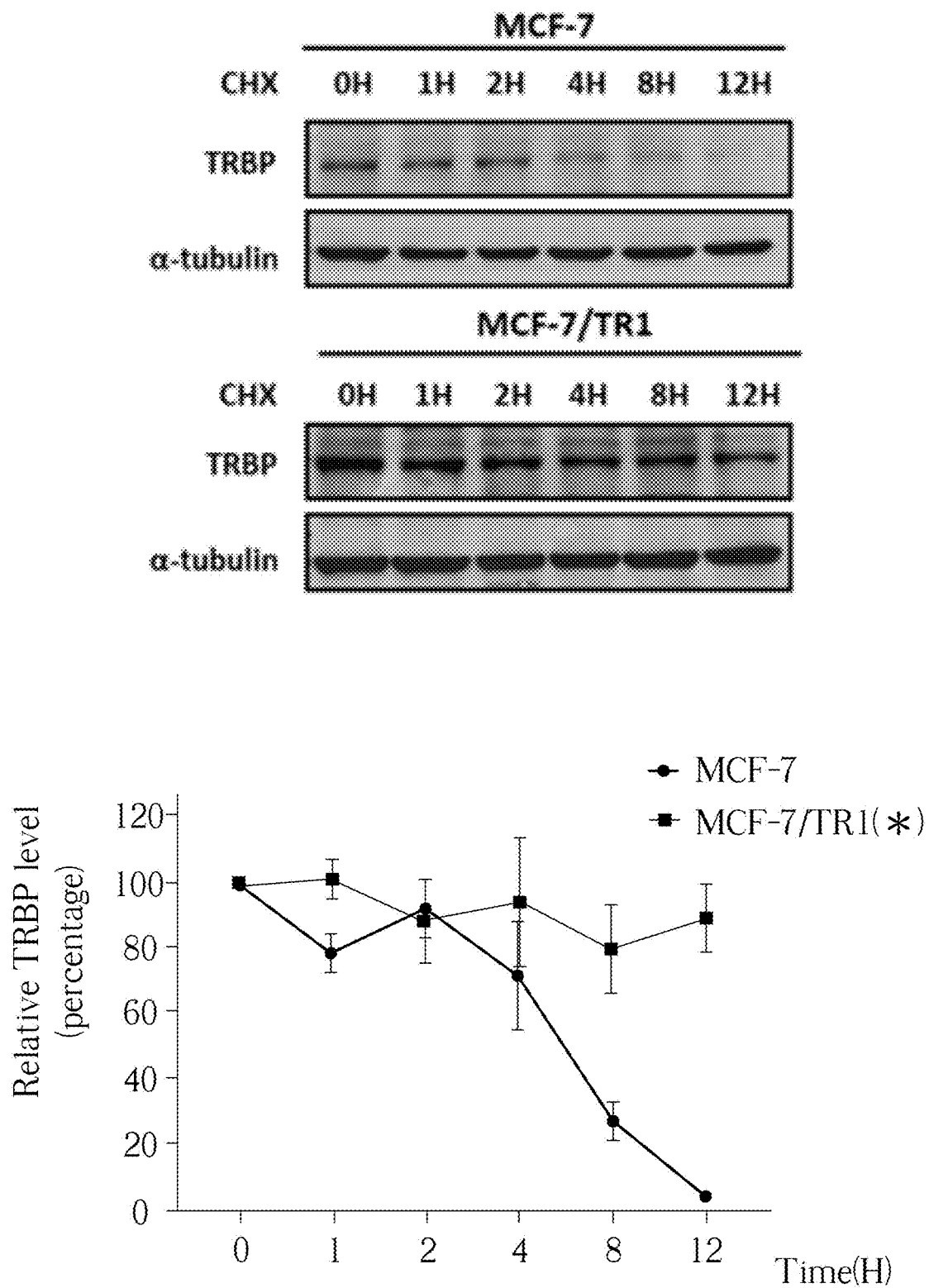

Next, the mechanism of tamoxifen-mediated TRBP induction was proved. Firstly, we analyzed the mRNA expression of TRBP and found that the TRBP mRNA level was not significantly changed either in the tamoxifen-resistant cell (MCF-7/TR) or in the tamoxifen-resistant cell (MCF-7/TR1), in which, RNA was isolated from the tamoxifen-resistant cell (MCF-7/TR) which was pretreated with 2 µM tamoxifen for 48 hours, and then seeded and cultured in plates until reaching 70-80% confluence in the presence of tamoxifen, to analyze a mRNA level of TRBP by a reverse-transcription PCR (qRTPCR). The aforementioned experiment was repeated at least 3 times, and the data thereof are shown in FIG. 7A, which suggested that the regulation of the TRBP protein expression may occur at the posttranscriptional level. Then, in order to investigate changes in TRBP protein stability, the mRNA expression of TRBP was analyzed by further treating the tamoxifen-resistant cell (MCF-7/TR) and the tamoxifen-resistant cell (MCF-7/TR1) with 50 µg/ml cycloheximide (CHX) to block de novo protein synthesis, followed by harvesting the tamoxifen-resistant cell (MCF-7/TR) and the tamoxifen-resistant cell (MCF-7/TR1) at an indicated time point to analyze the expression of TRBP in the tamoxifen-resistant cell (MCF-7/TR) and the tamoxifen-resistant cell through another western blot, wherein the degradation rates were plotted for the average±SEM of at least three independent experiments and analyzed by two-way ANOVA (*P≤0.05 and **P≤0.01). Accordingly, a significant prolonged degradation of TRBP protein was observed both in the tamoxifen-treated tamoxifen-sensitive cell (MCF-7) compared with an untreated tamoxifen-sensitive cell (MCF-7), as shown in FIG. 7B, and in the tamoxifen-treated tamoxifen-resistant cell (MCF-7/TR1) compared with an untreated tamoxifen-resistant cell (MCF-7/TR1), as shown in FIG. 7C. Thus, the above results indicate that tamoxifen treatment facilitates the accumulation of TRBP protein via a decrease in its degradation.

Figure 7D:
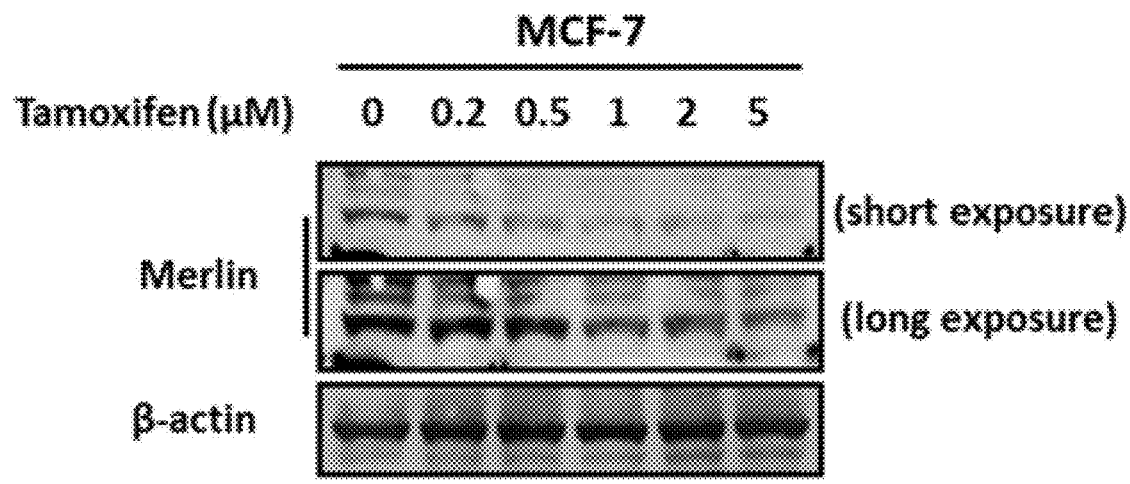
Figure 7E:
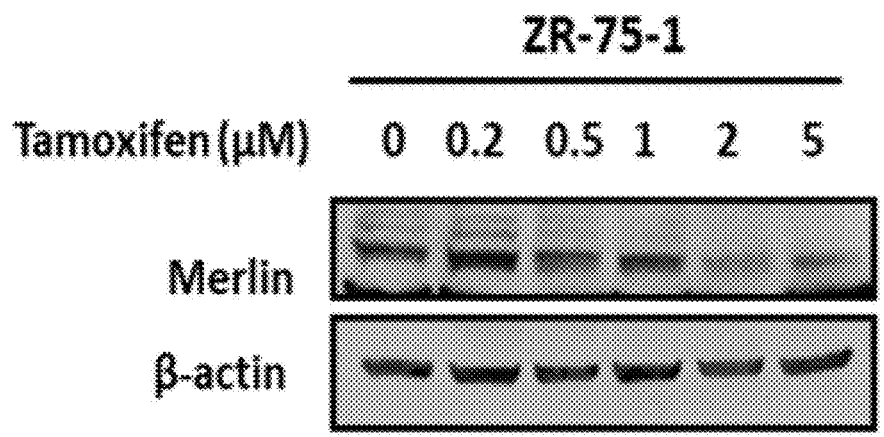

On the other hand, the present invention also proved that the expression of Merlin, as TRBP-interacting protein that promotes the ubiquitination and degradation of TRBP, was also suppressed in a dose-dependent manner in a tamoxifen-treated tamoxifen-sensitive cell (MCF-7) as shown in FIG. 7D and in a tamoxifen-treated ER+ breast cancer cell (ZR-75-1) as shown in FIG. 7E, in which, the tamoxifen-sensitive cell (MCF-7) and the ER+ breast cancer cell (ZR-75-1) were treated with increasing concentrations of tamoxifen for 48 hours, with the tamoxifen-sensitive cell (MCF-7) and the ER+ breast cancer cell (ZR-75-1) being transfected with indicated plasmid to overexpress Merlin for 24 hours, and then, another western blot was performed to detect the expression of TRBP and Merlin in the tamoxifen-sensitive cell (MCF-7) and the ER+ breast cancer cell (ZR-75-1). The above results suggest a possible mechanism in that tamoxifen inhibits Merlin to suppress TRBP protein degradation.

Figure 7F:
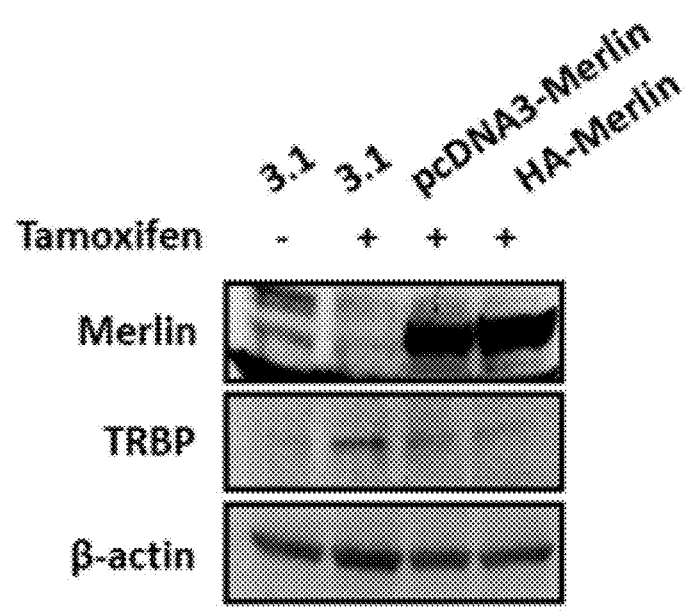
Figure 7G:
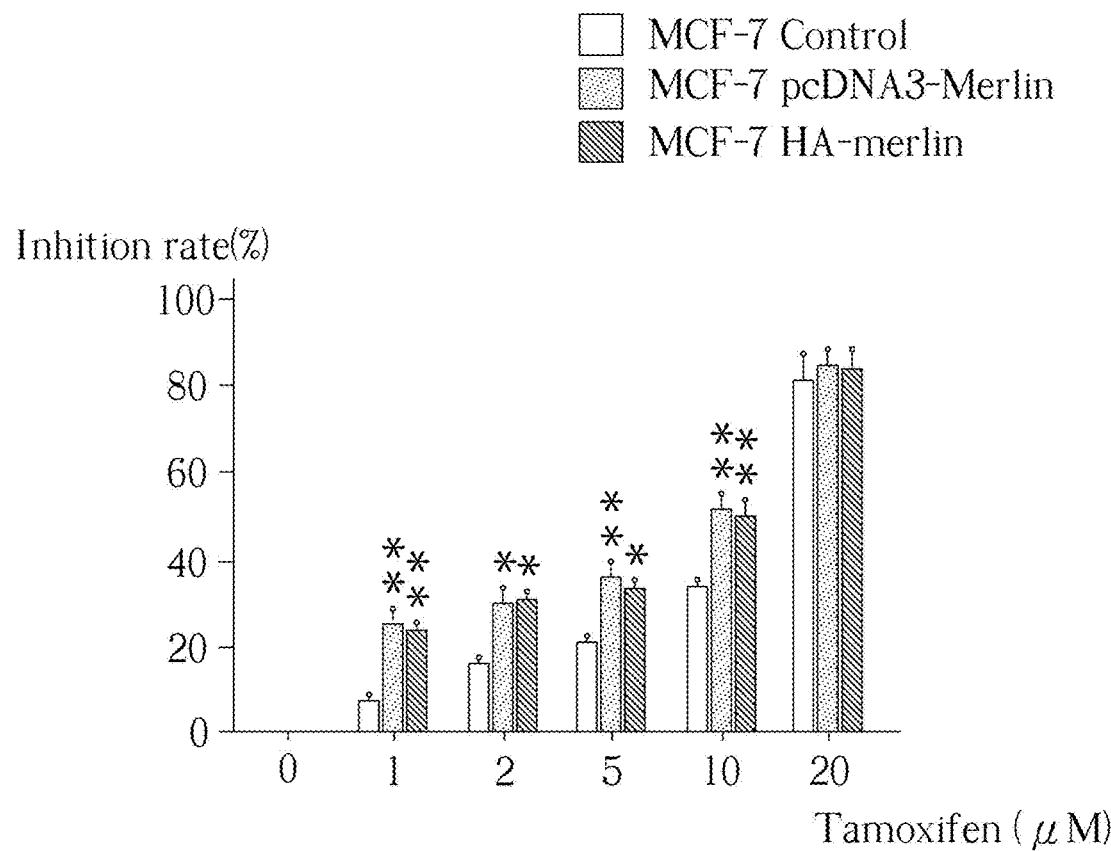
Figure 7H:
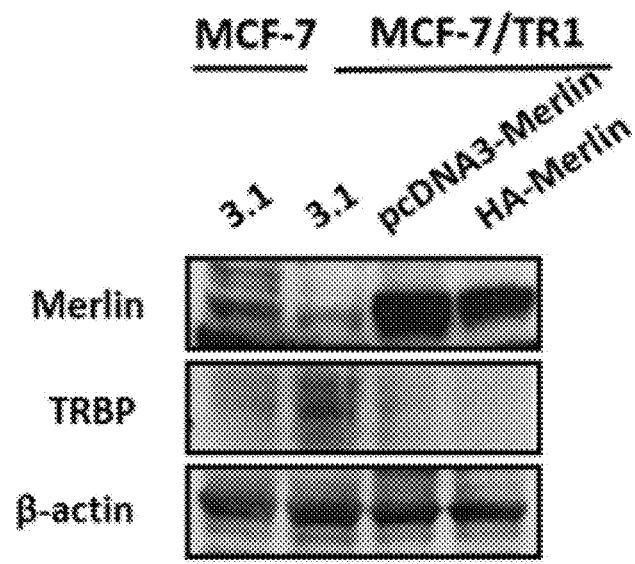

Next, we restored Merlin expression and determined TRBP expression in the tamoxifen-treated tamoxifen-sensitive cell (MCF-7) as shown in FIG. 7F and the tamoxifen-treated tamoxifen-resistant cell (MCF-7/TR1) as shown in FIG. 7H by transfected the tamoxifen-sensitive cell (MCF-7) and the tamoxifen resistant cell (MCF-7/TR1) with an indicated plasmid to overexpress Merlin for 24 hours and then collecting the tamoxifen-sensitive cell (MCF-7) and the tamoxifen resistant cell (TR1) to analyze the expression of TRBP and Merlin therein. Upon the restoration of Merlin, the upregulated TRBP was completely diminished both in the tamoxifen-treated tamoxifen-sensitive cell (MCF-7) as shown in FIG. 7F and in the tamoxifen-treated tamoxifen resistant cell (MCF-7/TR1) as shown in FIG. 7H.

Figure 7I:
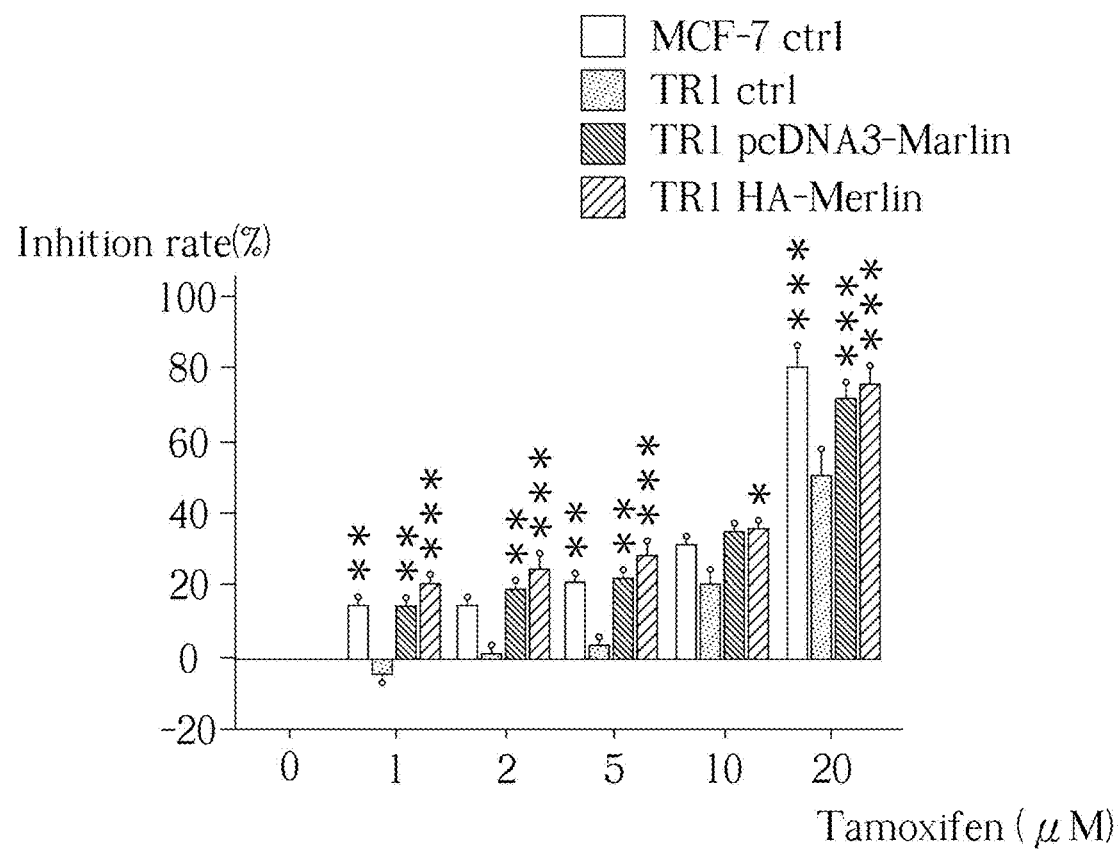

Then, the tamoxifen-sensitive cell (MCF-7) and the tamoxifen resistant cell (MCF-7/TR1) were further treated with different concentrations of tamoxifen (1, 2, 5, 10, 20 µM) for 72 h, and cell proliferations thereof were determined by another MTT assay, with data thereof being shown in FIGS. 7G and 7I, and with the MTT results being presented as the means±SEM from at least three separate experiments which were performed in duplicate or triplicate and analyzed by two-way ANOVA (*P≤0.05, P≤0.01, and *P≤0.001). Accordingly, the restoration of Merlin resensitized the tamoxifen-treated tamoxifen-sensitive cell (MCF-7) as shown in FIG. 7G and the tamoxifen-treated tamoxifen-resistant cell (MCF-7/TR1) as shown in FIG. 7I. Thus, the above results indicate that tamoxifen downregulates Merlin to stabilize the TRBP protein, which results in enhanced primary and acquired resistance to tamoxifen.

V. Tamoxifen-Induced TRBP Stabilizes SOX2 Protein to Enhance Desensitization of Breast Cancer Cells to Tamoxifen.

Figure 8A:
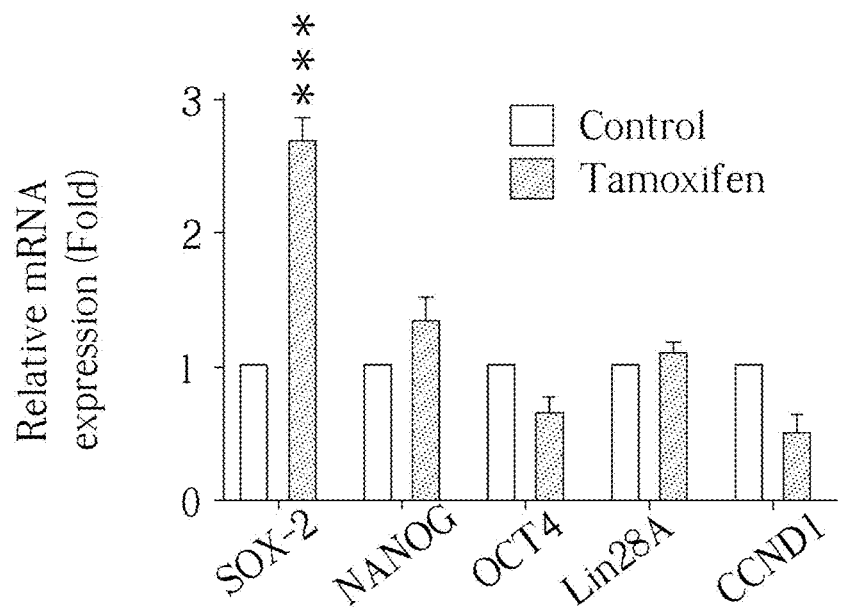
Figure 8B:
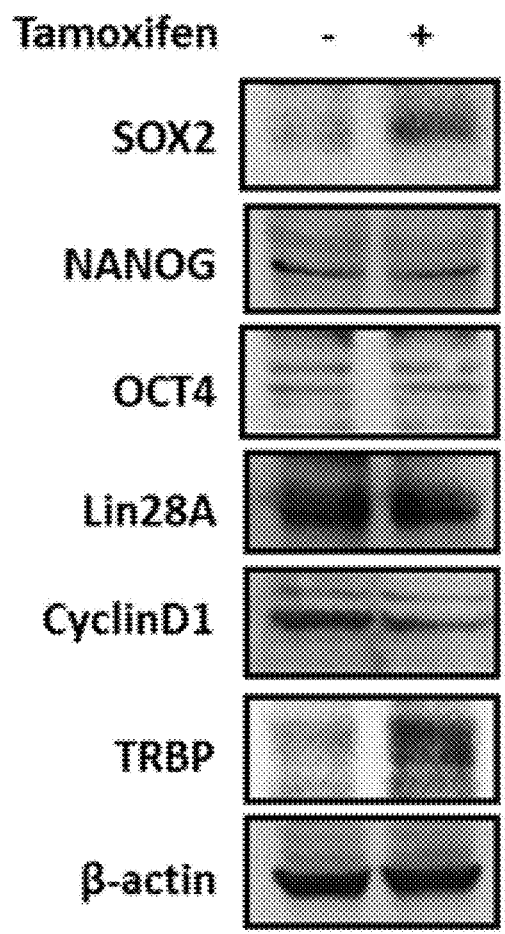

In order to identify the downstream modulator of TRBP, the tamoxifen-sensitive cells (MCF-7) were treated with 2 µM tamoxifen for 48 hours, and then RNA of the tamoxifen-sensitive cell (MCF-7) was isolated to analyze the mRNA expression of stem cell markers by using a reverse-transcription PCR (qRT-PCR), with the aforementioned experiment being repeated at least three times, and with ATP5E being used as a positive control for tamoxifen treatment (*P<0.05) by t-test. Then, the tamoxifen-sensitive cells (MCF-7) were further collected to analyze protein expression by using a western blot. Accordingly, we determined the expression of several key factors that have been reported to modulate self-renewal and drug resistance of cancer cells, including SOX2, Nanog, OCT4, Lin28A, CCND1. We used real-time qPCR to screen for the expression of these proteins and found that the expression of SOX2 mRNA was upregulated by tamoxifen treatment, as shown in FIG. 8A. The upregulated expression of SOX2 protein was further confirmed by the western blot as shown in FIG. 8B, with the reduction of cyclin D1 which is a known target inhibited by tamoxifen treatment as shown in FIGS. 8A and 8B.

Figure 8C:
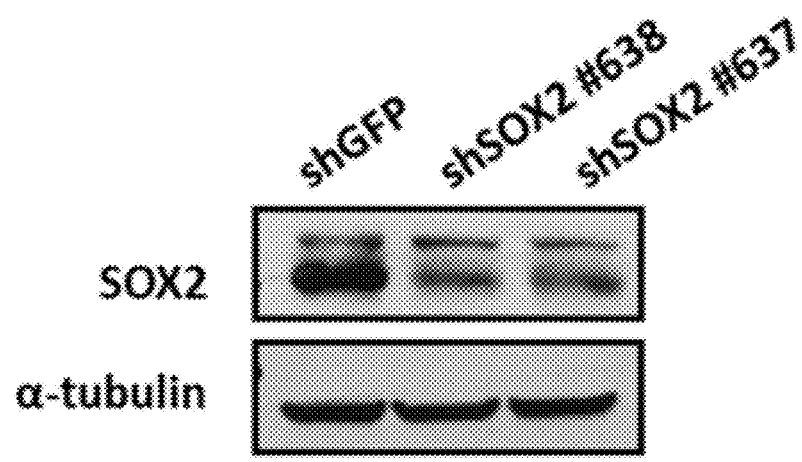
Figure 8D:
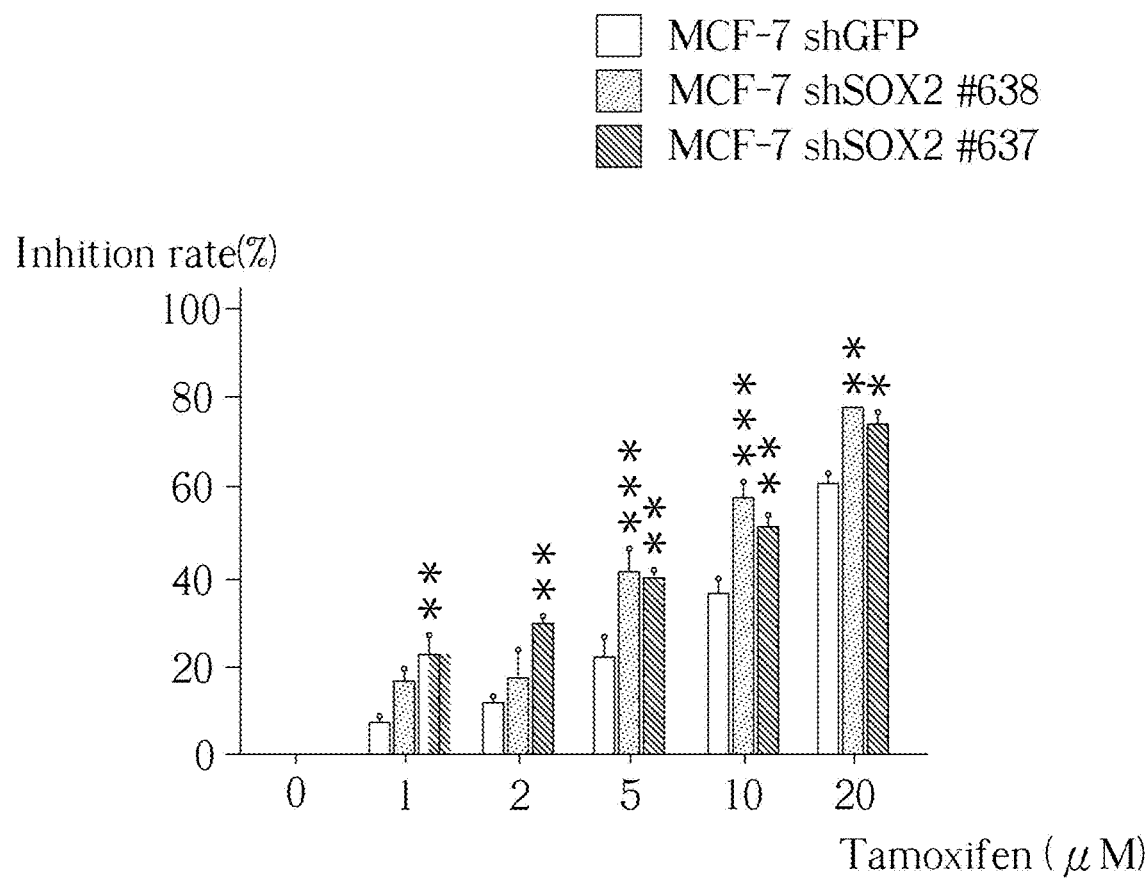
Figure 8E:
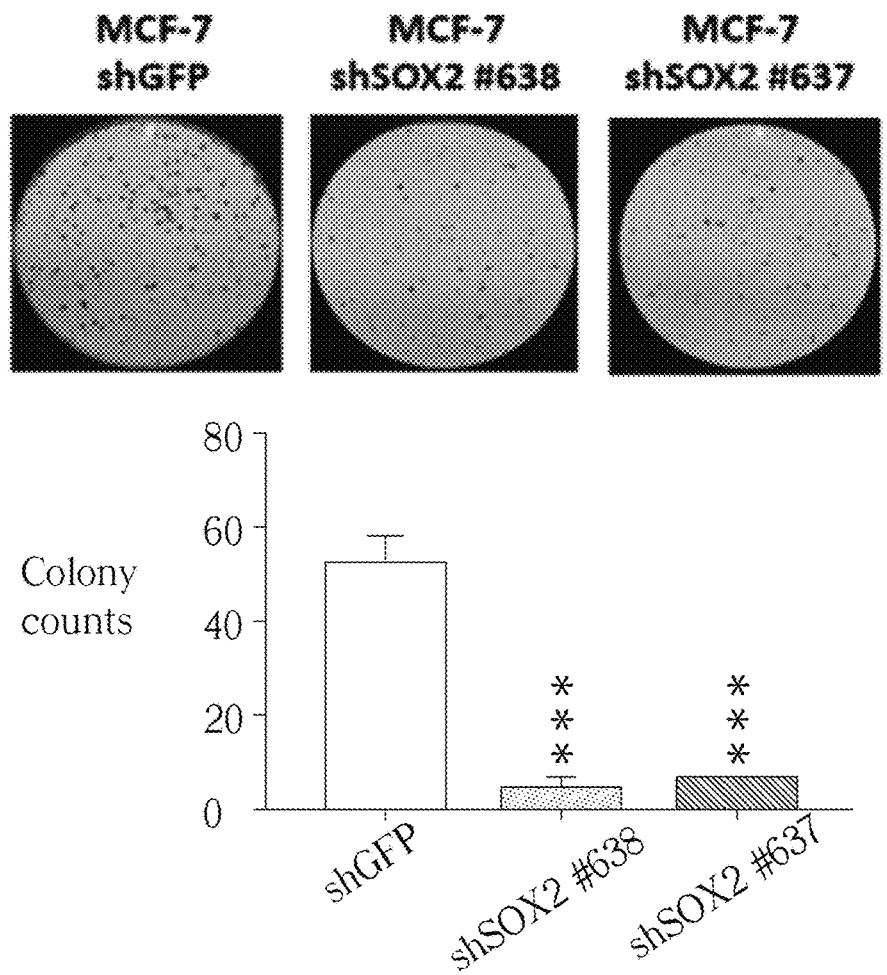

Then, in order to further identify the effect of SOX2 expression on tamoxifen sensitivity, the tamoxifen-sensitive cell (MCF-7) was transfected with shRNAs targeting SOX2 (including shSOX2 #638 and shSOX2 #637) for 48 hours and then treated with different concentrations of tamoxifen (1, 2, 5, 10, 20 µM) for 72 hours. The efficiency of SOX2 knock-down was examined by a western blot, and the proliferation and colony formation were determined by another MTT and another colony formation assays, respectively, with the MTT experimental results being given as the means±SEM from at least three separate experiments that were performed in duplicate or triplicate and analyzed by two-way ANOVA (*P≤0.05 and **P≤0.01). After the knock-down of SOX2 using the shRNAs (shSOX2 #638 and shSOX2 #637) as shown in FIG. 8C, the tamoxifen sensitivity of the tamoxifen-sensitive cell (MCF-7) was rescued according to the MTT data as shown in FIG. 8D and the colony formation data as shown in FIG. 6E, since the aforementioned data indicates the functional role of SOX2 in promoting tamoxifen resistance.

Figure 8F:
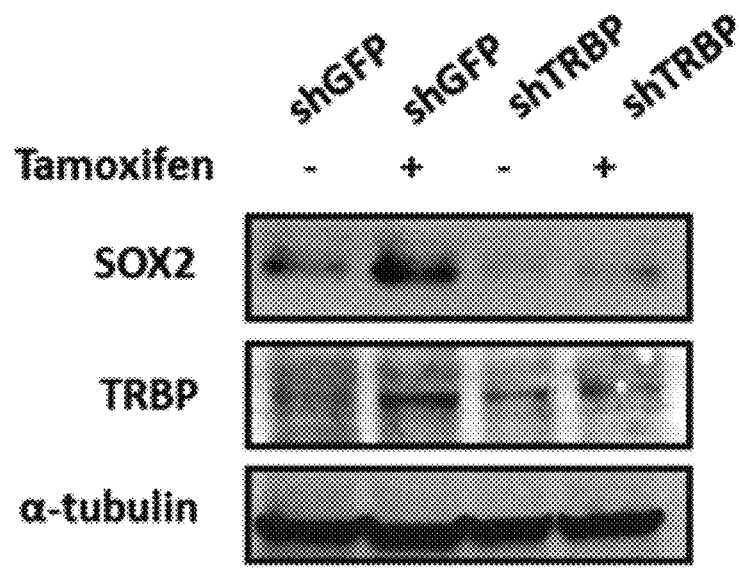
Figure 8G:
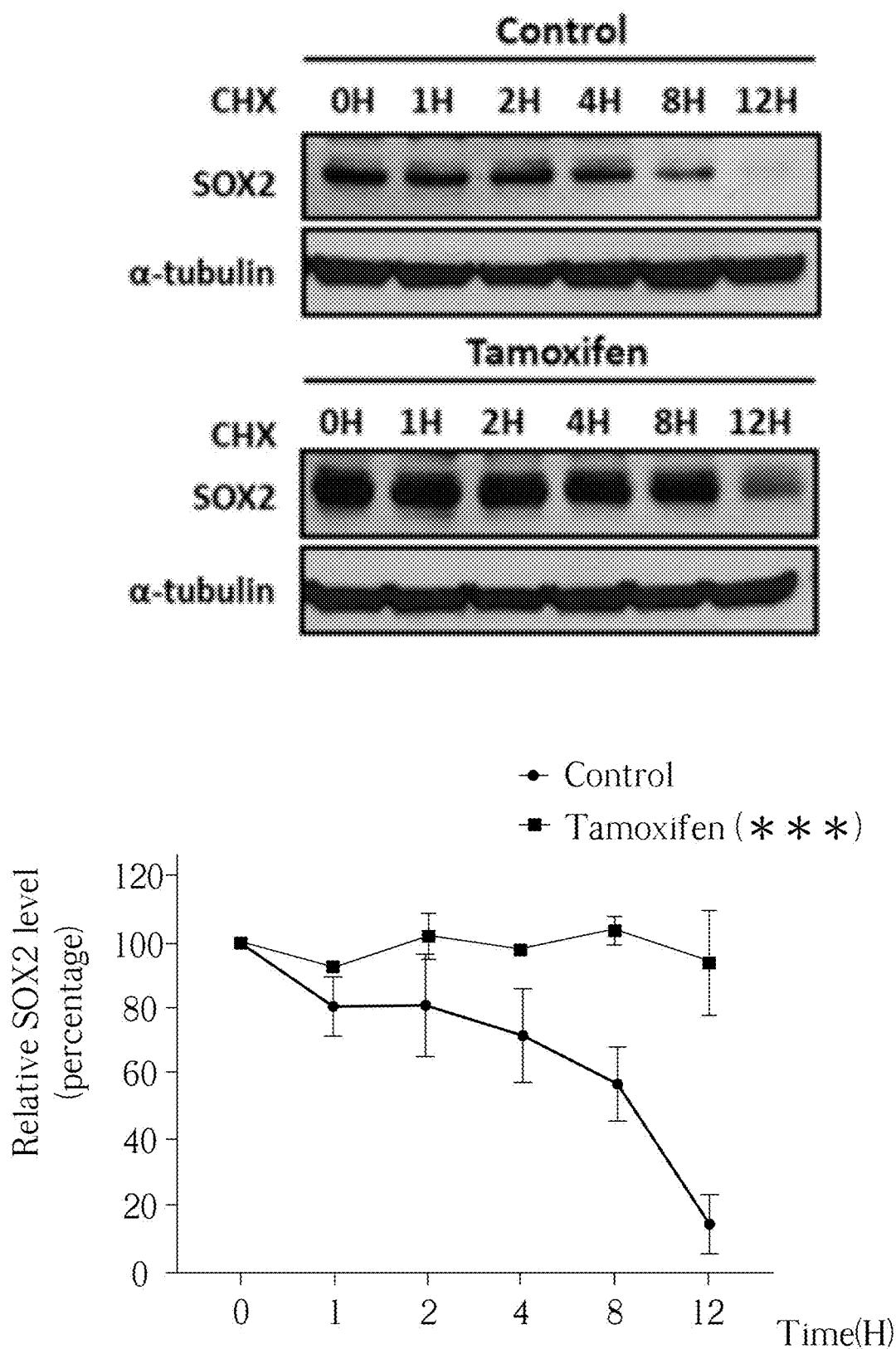
Figure 8H:
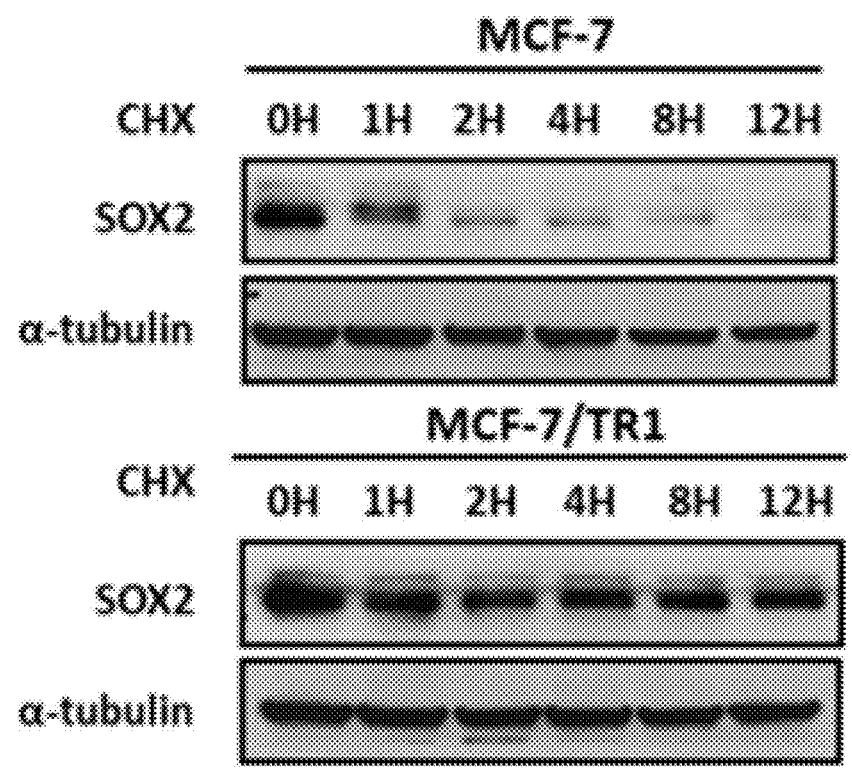
Figure 8H:
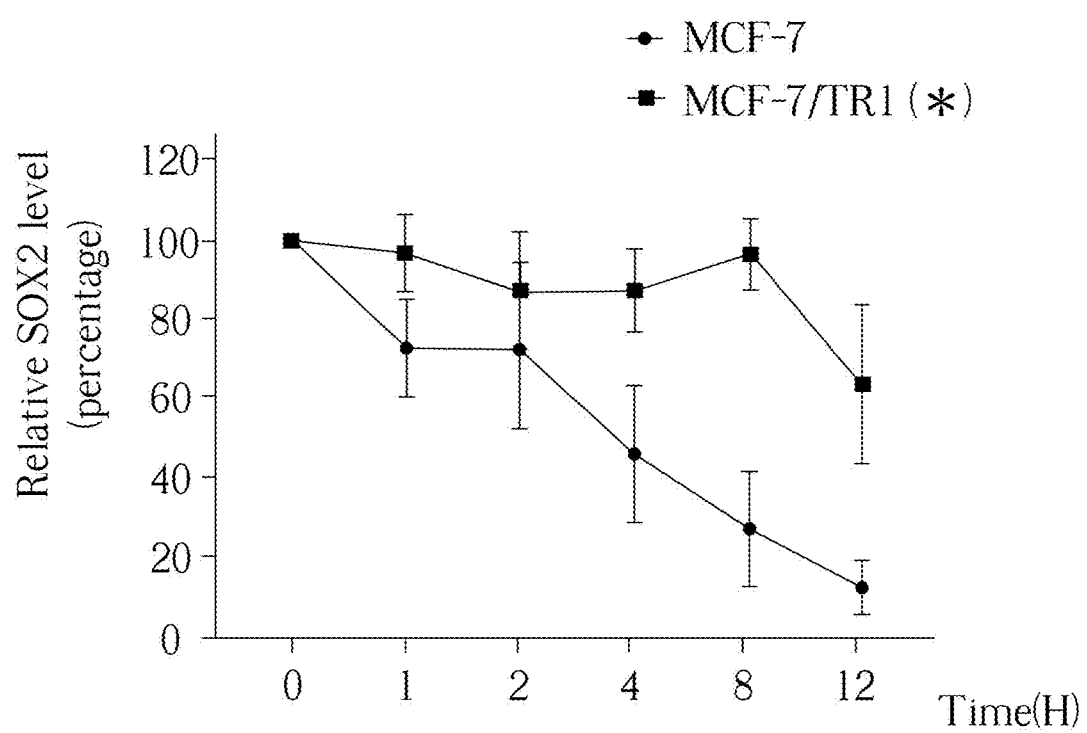
Figure 8I:
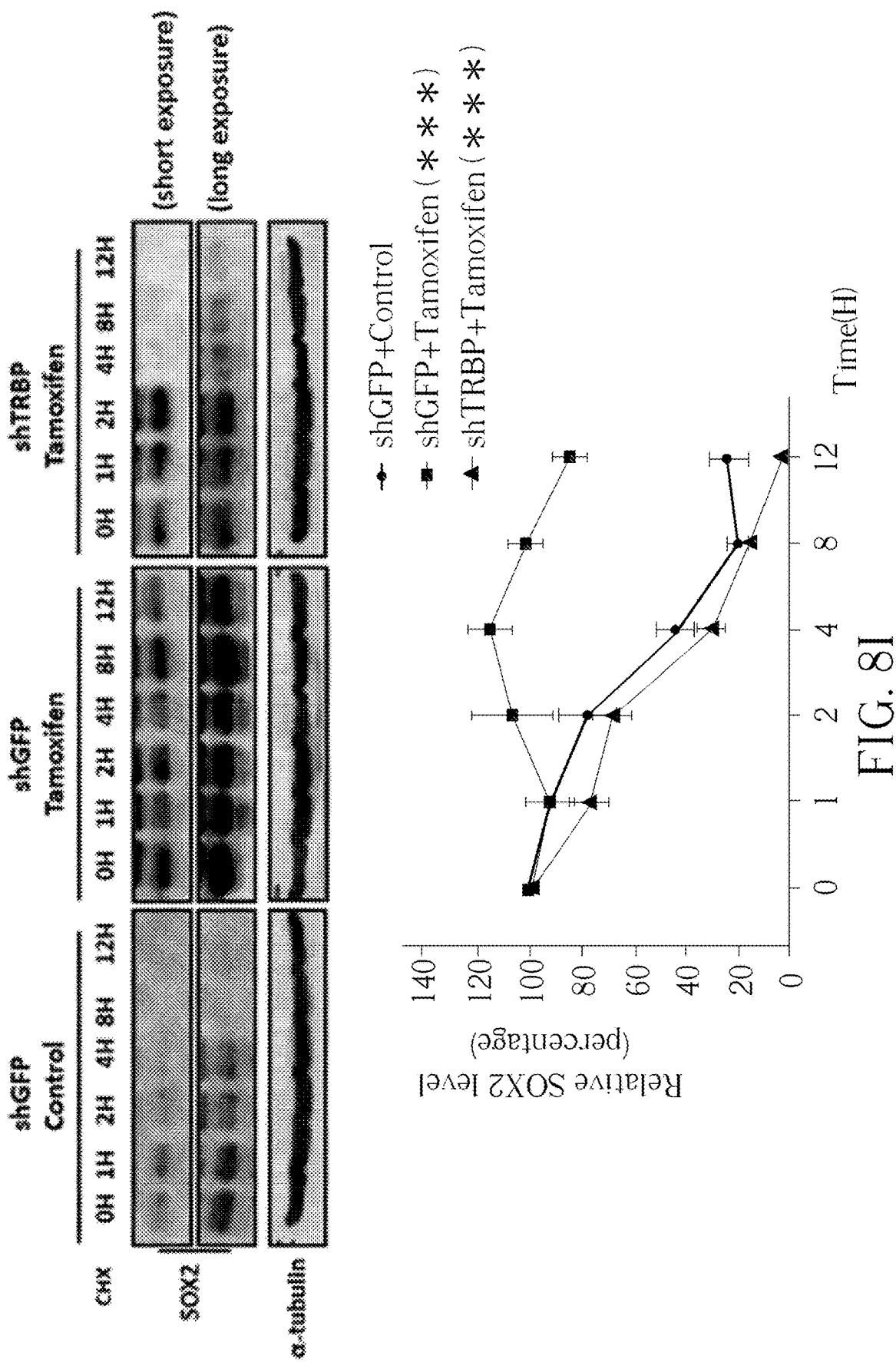

Next, in order to further prove tamoxifen downregulated the protein level of SOX2 through TRBP, the tamoxifen-sensitive cell (MCF-7) was transfected with the shRNAs targeting SOX2 (shSOX2 #638 and shSOX2 #637) for 48 hours, and the, 2 µM tamoxifen was added to a culture medium of the tamoxifen-sensitive cell (MCF-7) for 48 hours. After that, RNA was isolated from the tamoxifen-sensitive cell (MCF-7) to analyze the mRNA expression of SOX2 by using a reverse-transcription PCR (qRT-PCR). Accordingly, we found that tamoxifen also enhanced SOX2 expression as shown in FIG. 8F. Moreover, the induced SOX2 expression was completely abolished when TRBP was depleted in the tamoxifen-treated tamoxifen-sensitive cell (MCF-7) as shown in FIG. 8F, which indicates that the SOX2 accumulation is enhanced by tamoxifen-induced TRBP. The above results suggested that SOX2 is the functional downstream target of the tamoxifen-TRBP axis, which modulates drug resistance. Following these, we further examined SOX2 protein stability in the tamoxifen-treated tamoxifen-sensitive cell (MCF-7), the results thereof showed that SOX2 protein was degraded more slowly in the tamoxifen-treated tamoxifen-sensitive cell (MCF-7) compared with untreated tamoxifen-sensitive cell (MCF-7) as shown in FIG. 8G and in tamoxifen-treated tamoxifen-resistant cell (MCF-7/TR) compared with the untreated tamoxifen-resistant cell (MCF-7/TR) as shown in FIG. 8H. Furthermore, as shown in FIG. 8I, the depletion of TRBP in tamoxifen-treated tamoxifen-sensitive cell (MCF-7) blocked the tamoxifen-stabilized SOX2 protein accumulation. All these results suggest that SOX2 is a downstream factor that promotes tamoxifen resistance, which is regulated by tamoxifen-induced TRBP through posttranscriptional SOX2 protein stabilization.

Figure 8J:
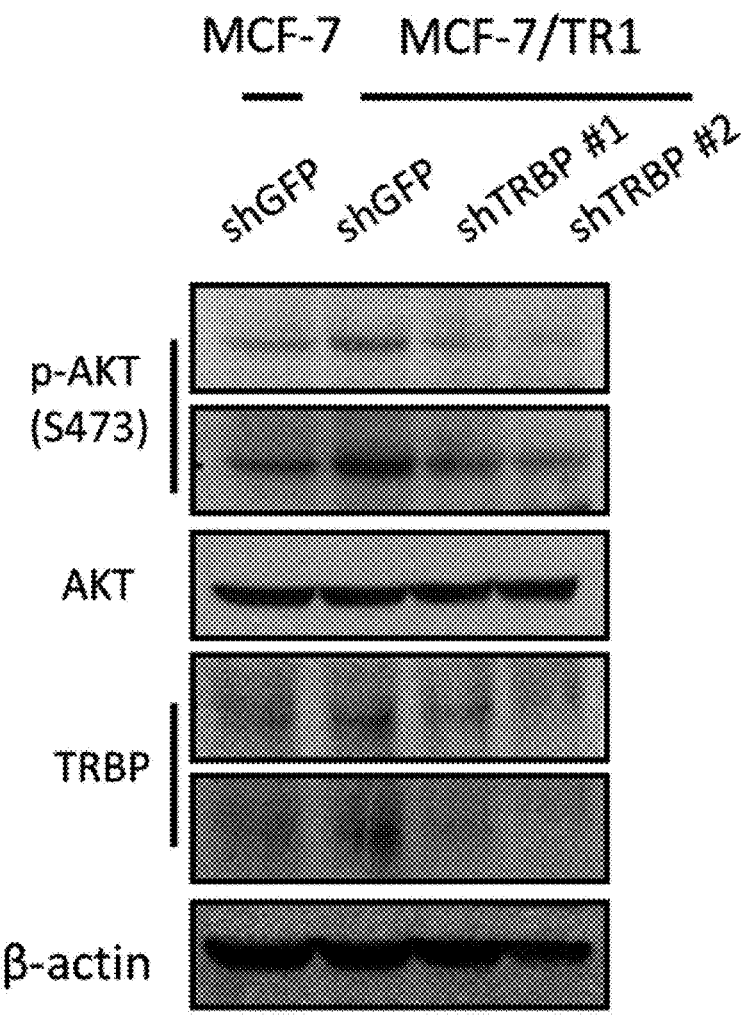
Figure 8K:
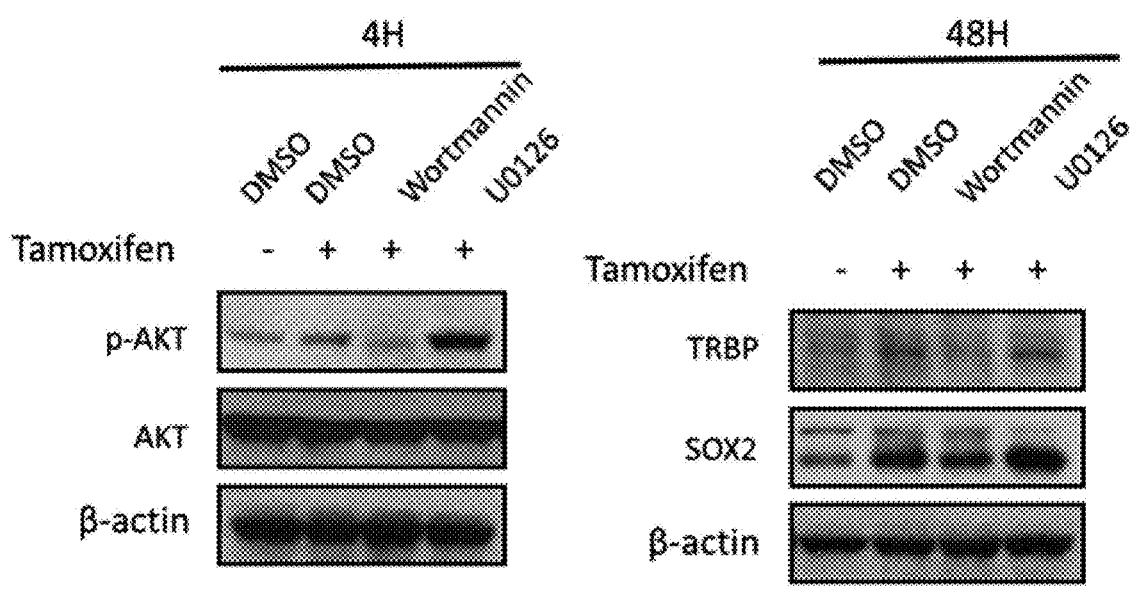

On the other hands, similar experiments above are also performed to identify the upstream modulator of TRBP. The results showed that p-AKT was obviously elevated in the tamoxifen-treated tamoxifen-resistant cell (MCF-7/TR1) compared with the tamoxifen-treated tamoxifen-sensitive cell (MCF-7) as shown in FIG. 8J. Also, after TRBP knockdown by shRNAs (such as shTRBP #1 and shTRBP #2), the enhanced p-AKT in the tamoxifen-treated tamoxifen-resistant cell (MCF-7/TR1) was suppressed, which suggests that a positive feedback regulation of TRBP-induced p-AKT. Furthermore, as shown in left of FIG. 8K, an elevated-AKT level was firstly observed after treated with tamoxifen, and then, an elevated-SOX2 level was then observed as shown in right of FIG. 8K. Also, inhibition of tamoxifen-induced p-AKT for example by using a P13K/AKT inhibitor like Wortmannin as shown in left of FIG. 8K blocked TRBP and SOX2 expression (as shown in right of FIG. 8K), which indicates that p-AKT induces TRBP-SOX pathway in the presence of tamoxifen. All these results suggest that p-AKT is an upstream factor that promotes tamoxifen resistance, which is regulated by a p-AKT-TRBP-SOX2 pathway.

Figure 9A:
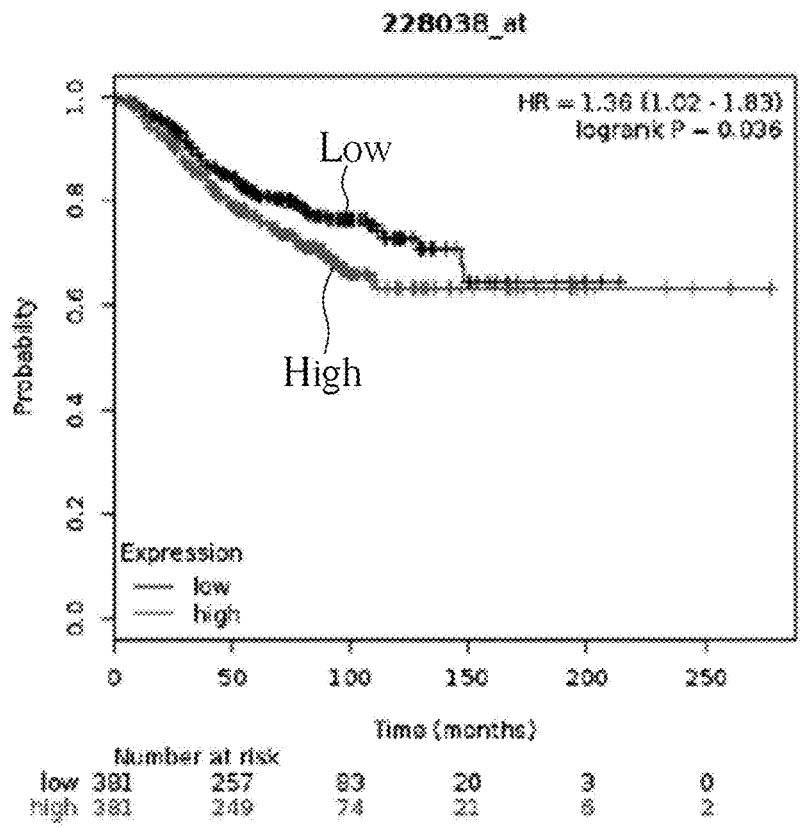
Figure 9B:
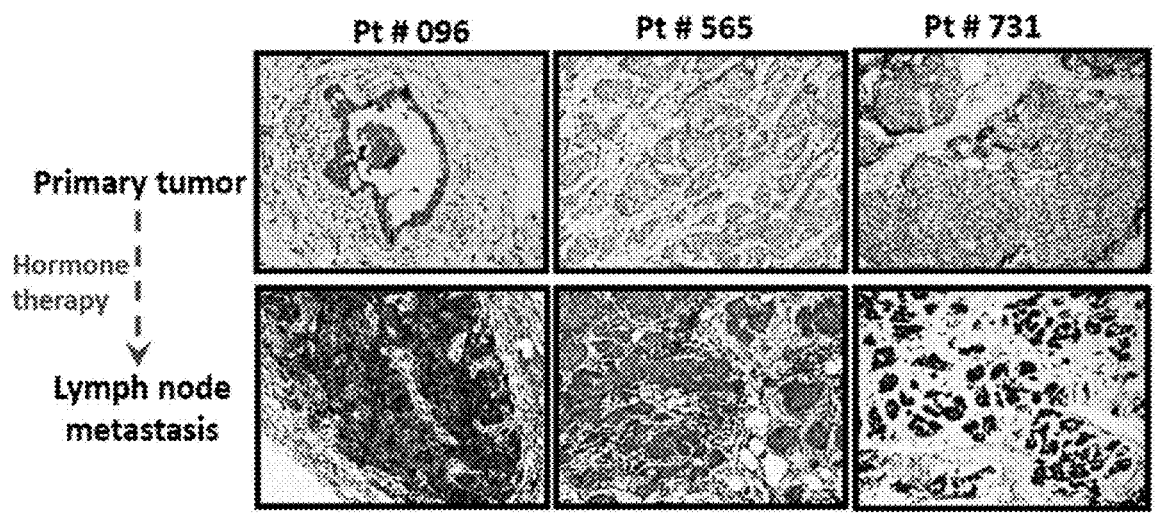
Figure 9C:
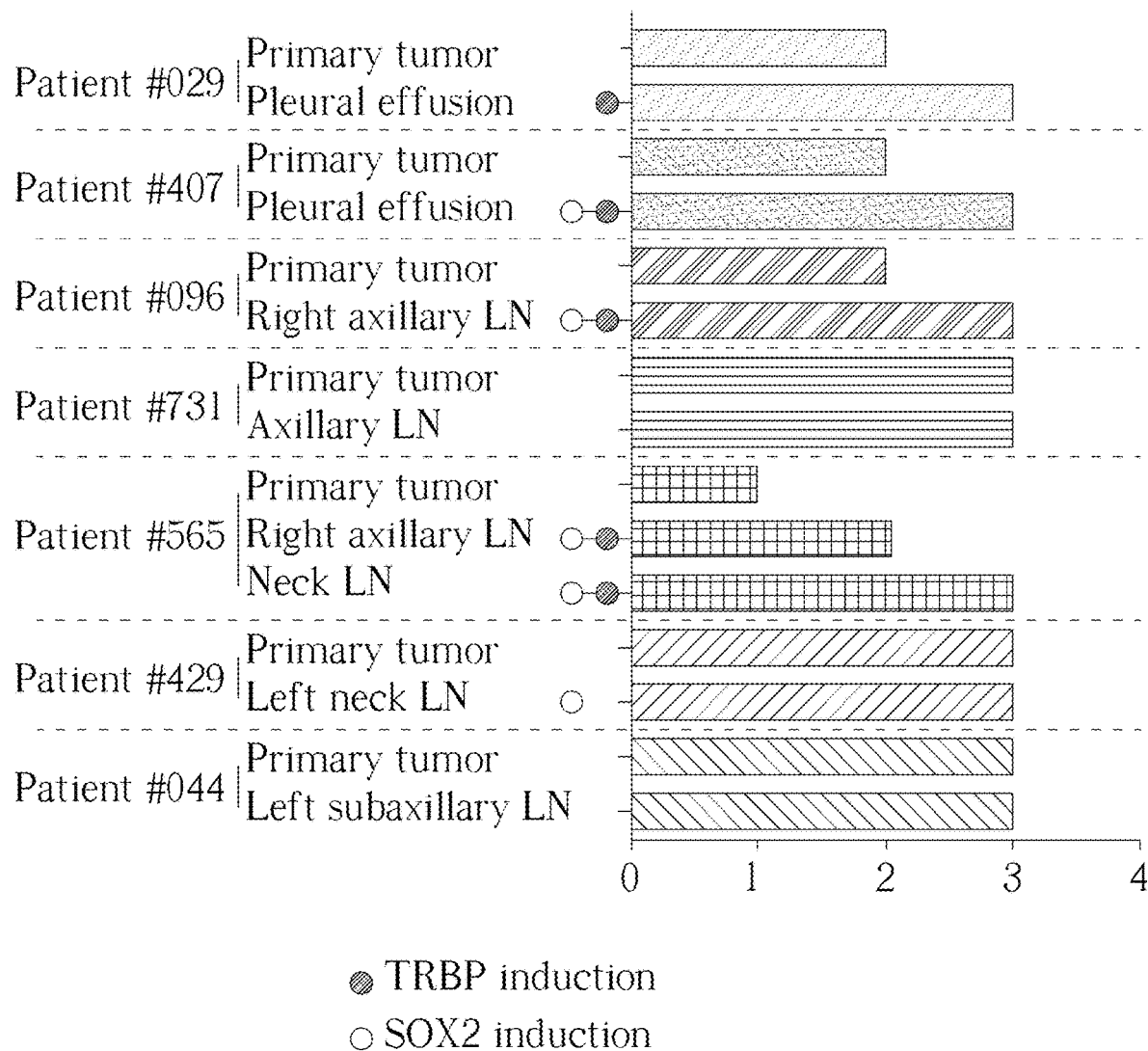

VI. Higher Expression of SOX2 is Correlated with the Level of TRBP and Hormone Therapy Resistance in Breast Cancer Patients In agreement with our findings that SOX2 is a downstream of TRBP that modulates tamoxifen resistance, we also observed that SOX2 expression is correlated with a poor prognosis of ER+ breast cancer patients, as shown in FIG. 9A. Precisely, the correlation of SOX2 expression with the overall survival of patients with ER+ breast cancer was analyzed and downloaded by using Kaplan-Meier Plotter. Also, to ensure the expression pattern of SOX2 protein in hormone therapy-resistant breast cancer tissues, we determined SOX2 expression by IHC. In the paired tumor tissues, five metastatic lymph nodes or pleural effusions showed enhanced SOX2 expression in comparison with the corresponding primary tumors, as shown in FIGS. 9B and 9C, while four of the five tissue pairs showed elevated TRBP expression as shown in FIGS. 9B, 9C and FIG. 1B, 1C. The above results support a vitro findings that TRBP upregulates SOX2, which in turn induces tamoxifen resistance, as well as poor prognosis.

Materials and Methods

Cell Culture:

Tamoxifen-sensitive cells (MCF-7) were cultured in low glucose Dulbecco's modified Eagle medium (DMEM) supplemented with 10% fetal bovine serum (FBS), 2% glutamine and 1% penicillin/streptomycin antibiotics. Tamoxifen-resistant cells (MCF-7/TR1, MCF-7/TR2, MCF-7/TR3) were established by culturing the tamoxifen-sensitive cells (MCF-7) in the presence of 3 µM tamoxifen over a period of 6 months. ER+ breast cancer cells were maintained in RPMI-1640 medium supplemented with 10% fetal bovine serum (FBS), 2% glutamine and 1% penicillin/streptomycin antibiotics. All cells were incubated at 37° C. with 5% $CO_2$ in a humidified incubator.

Western Blot:

Whole cell extracts were lysed in RIPA buffer and collected to fractionate by SDSPAGE, and then transferred onto PVDF membranes according to the manufacture's protocols (Bio-Rad). After blocking with 5% nonfat milk in TBST for 60 min, membranes were washed and incubated with primary antibodies at 4° C. overnight. Membranes were washed three times for 10 min and incubated with secondary antibodies for 60 min. Protein expressions were visualized by ECL system according to the manufacture's protocols.

RNA Extraction and Reverse Transcriptase Real-Time PCR (qRTPCR):

Total RNA was isolated by using Trizol reagent according to the manufacturer's instructions. 200 ng of RNA was reverse transcribed to complementary DNA (cDNA) by using a reverse transcriptase enzyme, a random primer, dNTPs and an RNase inhibitor. Real-time PCR was performed by Applied Biosystem Step One Real-time PCR system (Applied Biosystems) according to manufacturer's protocols. Samples run in three independent experiments and GAPDH or α-tubulin were used as an internal control to normalize the target genes.

MTT Assay:

Cell viability was analyzed by MTT (3, [4,5-dimethylthiazol-2-yl-]diphenyltetrazolium bromide, 5 mg/ml). Cells were seeding in 96-well plates and incubated overnight, and then changed into the fresh medium containing indicated concentrations of tamoxifen for 72 h. 50 µl of MTT was added to each well and incubated for 2 h, and the purple formazan crystals were dissolved in DMSO. The absorbance was measured by a microplate reader at a wavelength of 570 nm.

Colony Formation Assay:

$0.5 \times 10^3$ cells were seeded on the 6-well plates and incubated overnight, and 2 µM of tamoxifen was added to the medium for 7 days. The cells were fixed by 3.7% formaldehyde and stained by 0.05% crystal violet. The number of colonies was counted by Image J (NIH).

Patients and Specimens:

Breast cancer patients had operation for breast cancer and subsequently developed lymph node metastasis at National Taiwan University Hospital were included during 2011 to 2015. Paraffin-embedded, formalin-fixed surgical resection specimens were collected for immunohistochemical staining for TRBP and SOX2. All these patients had ER+ disease and had anti-hormone therapy for their disease. Tumor size, local invasion, and lymph node metastasis were acquired from pathology reports. Breast cancer tissues obtained from NTU Hospital were used according to IRB protocols approved by the NTU Hospital.

Immunohistochemistry:

Immunohistochemical studies were performed on formalinfixed, paraffin-embedded tissue. Tissue sections were deparaffinized according to established procedures Antigen retrieval was performed at pH9.0 using Epitope Retrieval 2 solution (Leica Microsystems) for 20 min at 100° C. The primary antibodies used were anti-SOX2 (Millipore, cat. AB5603, 1:50) anti-TRBP (Thermo, cat. LF-MA0209, Clone 46D1, 1:600) for 30 minutes. Slides were then stained using the Leica Microsystems BONDMAX autostainer according to the following steps. Post primary IgG linker reagent localized mouse antibody for 8 minutes. Poly-HRP IgG reagent localized rabbit antibody for 8 minutes. Staining was developed with the substrate chromogen, DAB for 10 minutes. The sections were counterstained with modified Mayer's hematoxylin for 5 minutes. The staining intensity was evaluated by pathologist.

Statistical Analysis:

All experiments were performed as the means±SEM. The Statistical significance between different groups was analyzed by one-way or two-way ANOVA in Prism 7 software. Values were considered significant when P value was less than 0.05.

Through the aforementioned experiments, it is shown that TRBP is overexpressed in tamoxifen-resistant cells and in cancer cells in metastatic lymph nodes of ER+ breast cancer patients after hormone therapy. Tamoxifen-induced TRBP expression resulted in the desensitization of ER+ breast cancer cells. Mechanistically, tamoxifen posttranscriptionally stabilizes the TRBP protein through downregulation of Merlin, a TRBP-interacting protein known to enhance its degradation via the ubiquitination-proteasome system. The tamoxifen-induced TRBP further stabilizes SOX2 protein to enhance desensitization of breast cancer cells to tamoxifen. Similar to TRBP expression, expression of SOX2 is also induced in cancer cells in metastatic lymph nodes of ER+ breast cancer patients after they received hormone therapy.

According to the present invention, the aforementioned p-AKT-TRBP-SOX2 pathway contributes not only to acquired resistance but also to de novo resistance, so that, the evaluating method for a hormone therapy in breast cancer may be established thereby, through measuring and monitoring a level change of TRBP in a target subject to discriminate the acquired resistance and/or the novo resistance, and also to further determine recurrence and/or poor prognosis of breast cancer. Precisely, in the evaluating method for a hormone therapy in breast cancer, a primary level of TRBP in the target subject and a level of TRBP in the target subject taken after the tamoxifen treatment are both collected from the target subject, and the level change between the primary level and the level of TRBP in the target subject is monitored to discriminate the acquired resistance and/or the novo resistance in the target subject. While the level of TRBP is higher than the primary level of TRBP in the target subject, such as being about 20% or more than 20% higher than the primary level of TRBP, the target subject is discriminated as the acquired resistance and/or primary resistance. Also, while the level of TRBP is higher than the primary level of TRBP in the target subject, such as being about 10%-90% higher than the primary level of TRBP, the target subject is discriminated to have recurrence and/or poor prognosis of breast cancer.

Furthermore, according to the aforementioned p-AKT-TRBP-SOX2 pathway of the present invention, the induction of TRBP which is triggered by the tamoxifen treatment may further suggest an unexpected effect of tamoxifen during hormone therapy, and the evaluating method of the present invention therefore reveals a missing link between the tamoxifen-induced signaling network and tamoxifen resistance, which provides important information for the design of better therapeutic approaches in breast cancer.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of evaluating drug resistance in hormone therapy, comprising:
   measuring a primary level of TAR human immunodeficiency virus-1 RNA binding protein 2 (TRBP) in a first sample taken from a subject;
   administrating an effective amount of tamoxifen, an active form of tamoxifen or an analogous of tamoxifen to the subject;
   after providing the tamoxifen, the active form of tamoxifen or the analogous of tamoxifen to the subject, measuring a level of TRBP in a second sample taken from the subject; and
   discriminating tamoxifen resistance through a level change between the level of TRBP in the second sample taken from the subject and the primary level of TRBP in the first sample taken from the subject.

2. The method of evaluating drug resistance in hormone therapy according to claim 1, further comprising:
   after providing the tamoxifen, the active form of tamoxifen or the analogous of tamoxifen to the subject, measuring a level of SRY-Box transcription factor (SOX2) in a third sample of the subject; and
   discriminating tamoxifen resistance also through comparing a level change of SOX2 between a primary level of SOX2 in the first sample taken from the subject and the level of SOX2 in the third sample taken from the subject.

3. The method of evaluating drug resistance in hormone therapy according to claim 2, wherein the level change of SOX2 comprises a protein level change of SOX2 between the third sample and the first sample taken from in the subject.

4. The method of evaluating drug resistance in hormone therapy according to claim 1, further comprising:
   measuring a level of phosphorylate Akt (p-AKT) in a fourth sample taken from the subject; and
   discriminating the tamoxifen resistance also through comparing a level change of p-AKT between a primary level of p-AKT in the first sample taken from the subject and the level of p-AKT in the fourth sample taken from the subject.

5. The method of evaluating drug resistance in hormone therapy according to claim 1, wherein the level change of TRBP is between the primary level of TRBP and the level of TRBP.

6. The method of evaluating drug resistance in hormone therapy according to claim 5, wherein the level change of TRBP comprises a protein level change of TRBP in the subject.

7. The method of evaluating drug resistance in hormone therapy according to claim 5, wherein the level change of TRBP is 20% or more than 20%.

8. The method of evaluating drug resistance in hormone therapy according to claim 1, wherein the active form of tamoxifen comprises 4-hydroxytamosifen.

9. The method of evaluating drug resistance in hormone therapy according to claim 1, wherein the effective amount of the active form of tamoxifen is 20-40 mg/per day.

10. The method of evaluating drug resistance in hormone therapy according to claim 1, wherein the administrating of the tamoxifen is carried out through an injection, an oral administration or an incubation.

11. The method of evaluating drug resistance in hormone therapy according to claim 1, wherein the effective amount of the tamoxifen is 20-40 mg/per day.

12. The method of evaluating drug resistance in hormone therapy according to claim 1, further comprising:
    determining prognosis of cancer through the level change of TRBP in the subject.

13. The method of evaluating drug resistance in hormone therapy according to claim 12, further comprising:
    measuring a level of SRY-Box transcription factor (SOX2) in a third sample taken from the subject; and
    discriminating the prognosis of cancer also through comparing a level change of SOX2 between a primary level of SOX2 in the first sample taken from the subject and the level of SOX2 in the third sample taken from the subject.

14. The method of evaluating drug resistance in hormone therapy according to claim 13, further comprising:
    measuring a level of phosphorylated AKT (p-AKT) in a fourth sample taken from the subject; and
    discriminating the prognosis of cancer also through comparing a level change of p-AKT between a primary level of p-AKT in the first sample taken from the subject and the level of p-AKT in the fourth sample taken from the subject.

15. The method of evaluating drug resistance in hormone therapy according to claim 1, further comprising:
    determining recurrence of cancer through the level change of TRBP in the subject.

16. The method of evaluating drug resistance in hormone therapy according to claim 15, further comprising:
    measuring a level of SOX2 in a third sample taken from the subject; and
    discriminating the recurrence of cancer also through comparing a level change of SOX2 between a primary level of SOX2 in the first sample taken from the subject and the level of SOX2 in the third sample taken from the subject.

17. The method of evaluating drug resistance in hormone therapy according to claim 16, further comprising:
    measuring a level of p-AKT in a fourth sample taken from the subject; and
    discriminating the recurrence of cancer also through comparing a level change of p-AKT between a primary level of p-AKT in the first sample taken from the subject and the level of p-AKT in the fourth sample taken from the subject.

\* \* \* \* \*